United States Patent
West, Jr. et al.

(10) Patent No.: US 8,029,537 B2
(45) Date of Patent: Oct. 4, 2011

(54) KNOTLESS SUTURE ANCHOR AND METHOD FOR KNOTLESSLY SECURING TISSUES

(75) Inventors: Hugh Sloan West, Jr., Salt Lake City, UT (US); Lehmann K. Li, Milford, CT (US)

(73) Assignee: Linvatec Corporation, Largo, FL (US)

( * ) Notice: Subject to any disclaimer, the term of this patent is extended or adjusted under 35 U.S.C. 154(b) by 0 days.

(21) Appl. No.: 12/644,891

(22) Filed: Dec. 22, 2009

(65) Prior Publication Data

US 2010/0100126 A1    Apr. 22, 2010

Related U.S. Application Data

(62) Division of application No. 10/661,135, filed on Sep. 11, 2003, now Pat. No. 7,662,171, which is a division of application No. 09/995,288, filed on Nov. 26, 2001, now Pat. No. 6,692,516.

(60) Provisional application No. 60/253,534, filed on Nov. 28, 2000.

(51) Int. Cl.
*A61B 17/04* (2006.01)

(52) U.S. Cl. ............................. 606/232; 623/13.14

(58) Field of Classification Search .............. 606/72–73, 606/144, 148, 151, 232, 228; 623/13.14
See application file for complete search history.

(56) References Cited

U.S. PATENT DOCUMENTS

| | | |
|---|---|---|
| 4,738,255 A | 4/1988 | Goble et al. |
| 4,750,492 A | 6/1988 | Jacobs |
| 5,207,679 A | 5/1993 | Li |
| 5,336,240 A | 8/1994 | Metzler et al. |
| 5,545,180 A | 8/1996 | Le et al. |
| 5,562,686 A | 10/1996 | Sauer et al. |
| 5,645,589 A | 7/1997 | Li |
| 5,690,649 A | 11/1997 | Li |
| 5,716,368 A | 2/1998 | de la Torre et al. |

(Continued)

FOREIGN PATENT DOCUMENTS

EP    1 202 672    3/2004

(Continued)

OTHER PUBLICATIONS

Surgical Technique Review: Arthroscopic Bankart Repair "Bioknotless Anchor Absorbable Suture Anchor"—Mitek Products, Ethicon 3 page advertisement.

*Primary Examiner* — Victor Nguyen
(74) *Attorney, Agent, or Firm* — Ostrolenk Faber LLP

(57) ABSTRACT

A method for securing first and second tissues with a suture anchor. The method includes forming a borehole in the first tissue; threading a suture through the second tissue forming a loop in the suture with the tissue thereby secured in the loop, the loop defining two suture portions; attaching the two suture portions to the anchor whereby the two suture portions are threaded through the anchor and initially movable with respect to the anchor; and providing a force to a shaft of the anchor, the force causing clamping of the two suture portions in the anchor and deformation of a deformable portion of the anchor to cause the deformable portion to engage a wall of the borehole thereby to secure the suture anchor in the first tissue and the loop holding the second tissue to the suture anchor.

3 Claims, 34 Drawing Sheets

U.S. PATENT DOCUMENTS

| | | |
|---|---|---|
| 5,725,541 A | 3/1998 | Anspach et al. |
| 5,741,300 A | 4/1998 | Li |
| 5,814,071 A | 9/1998 | McDevitt et al. |
| 5,843,087 A | 12/1998 | Jensen et al. |
| 5,843,127 A | 12/1998 | Li |
| 5,902,321 A | 5/1999 | Caspari et al. |
| 5,948,000 A | 9/1999 | Larsen et al. |
| 5,948,001 A | 9/1999 | Larsen |
| 5,957,953 A | 9/1999 | DiPoto et al. |
| 6,022,373 A | 2/2000 | Li |
| 6,045,574 A | 4/2000 | Thal |
| 6,086,608 A | 7/2000 | Ek et al. |
| 6,117,144 A | 9/2000 | Nobles et al. |
| 6,129,762 A | 10/2000 | Li |
| 6,143,017 A * | 11/2000 | Thal ................ 606/232 |
| 6,149,669 A * | 11/2000 | Li ................ 606/232 |
| 6,156,039 A | 12/2000 | Thal |
| 6,200,329 B1 | 3/2001 | Fung et al. |
| 6,221,107 B1 | 4/2001 | Steiner et al. |
| 6,231,592 B1 | 5/2001 | Bonutti et al. |
| 6,355,053 B1 | 3/2002 | Li |
| 6,524,317 B1 | 2/2003 | Ritchart et al. |
| 6,692,516 B2 * | 2/2004 | West et al. ................ 606/232 |

FOREIGN PATENT DOCUMENTS

| | | |
|---|---|---|
| FR | 2 784 020 | 4/2000 |
| WO | WO 01/62160 | 8/2001 |
| WO | WO 02/21999 | 3/2002 |

* cited by examiner

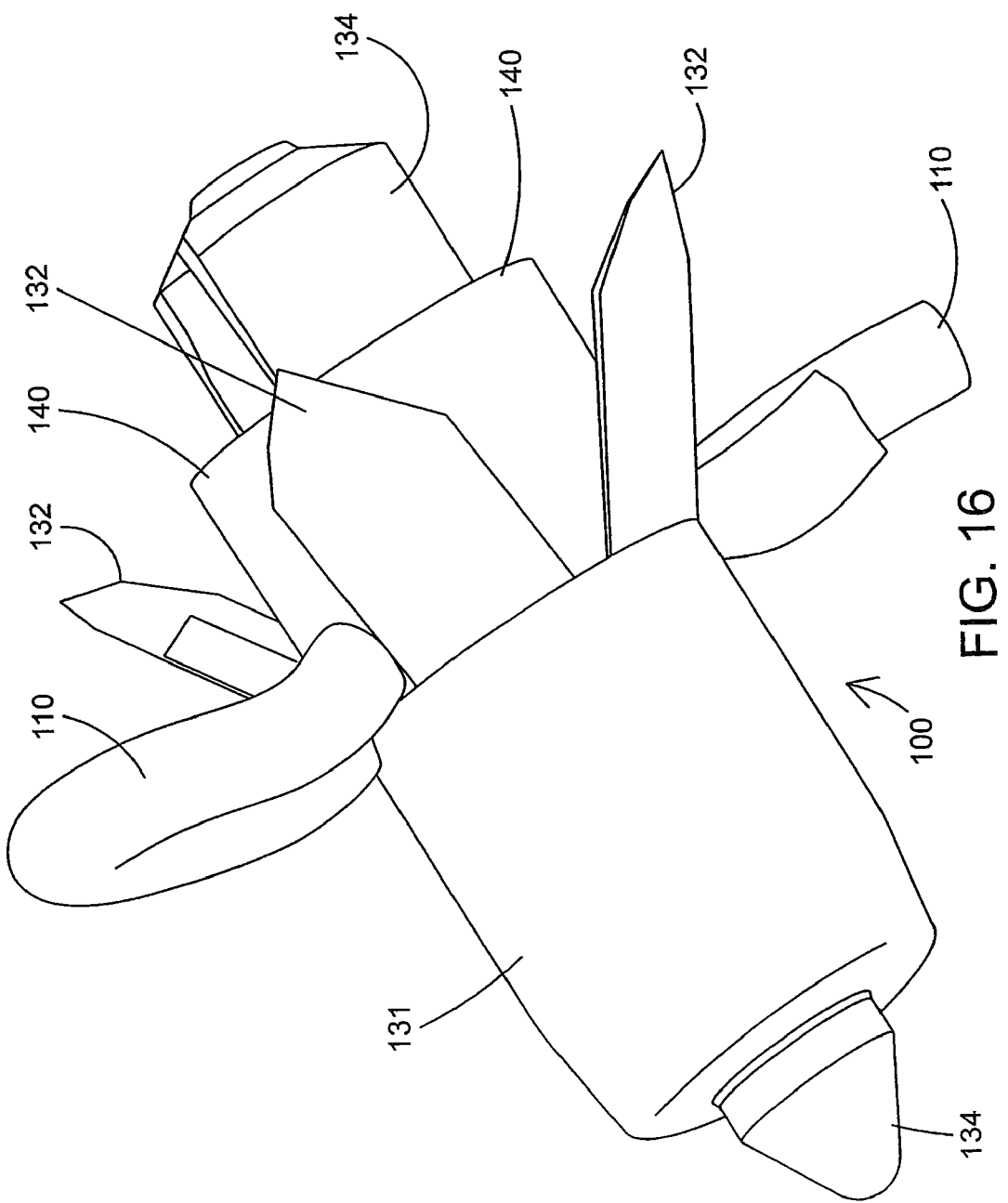

SECTION E-E

SECTION E-E

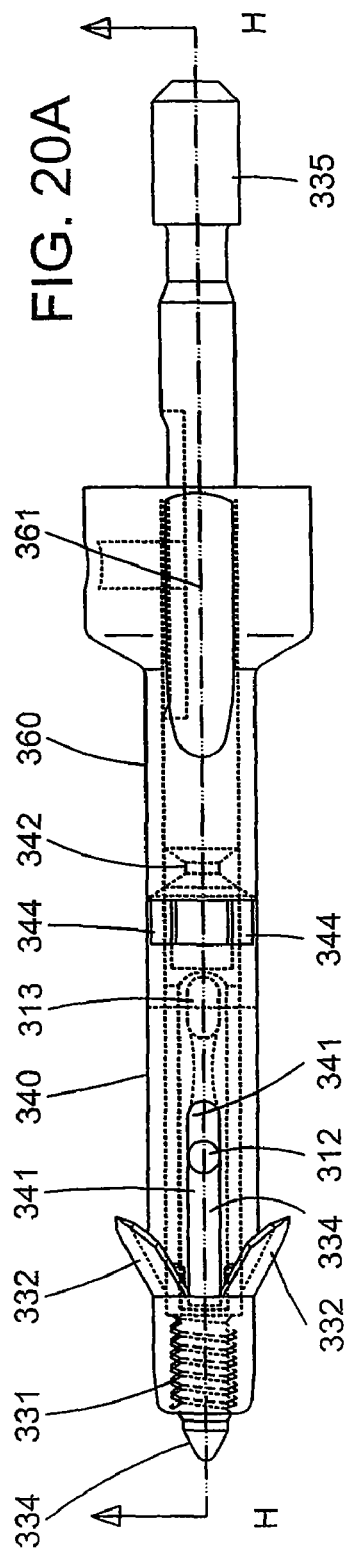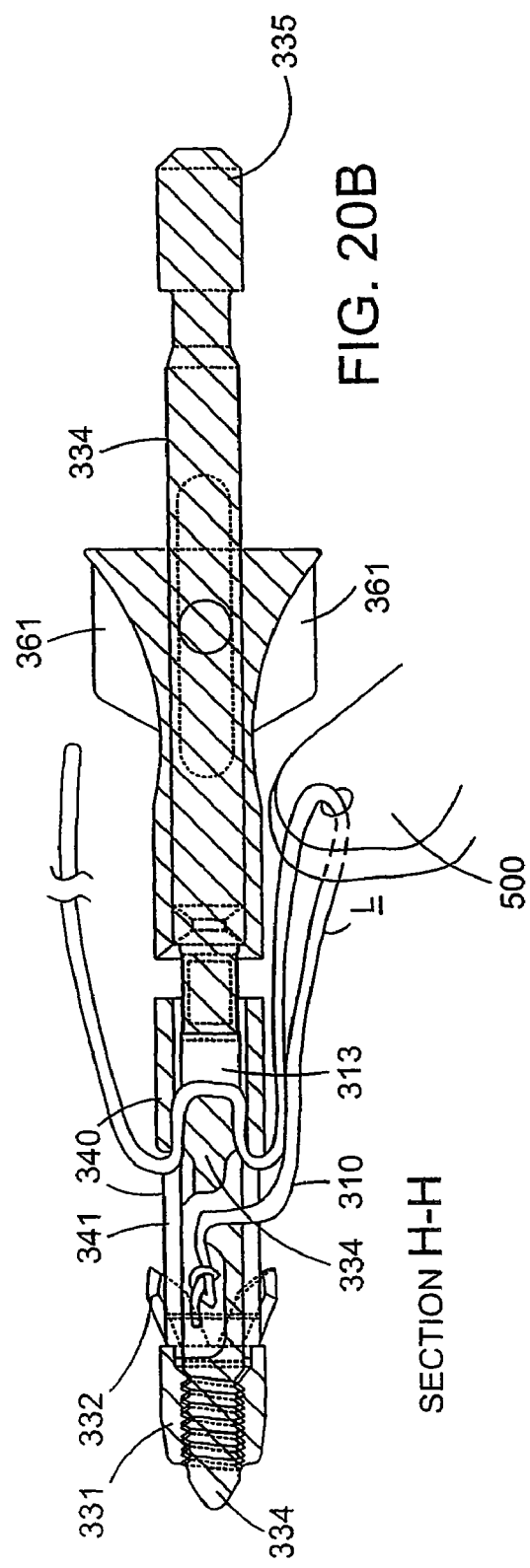

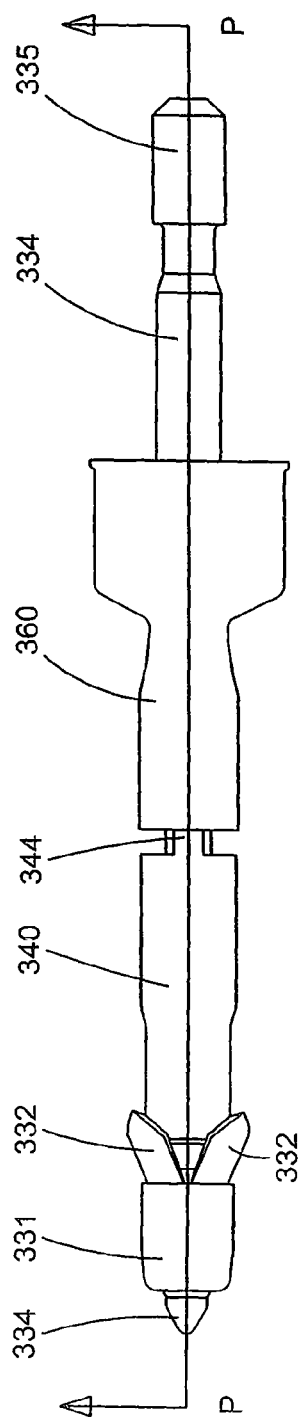
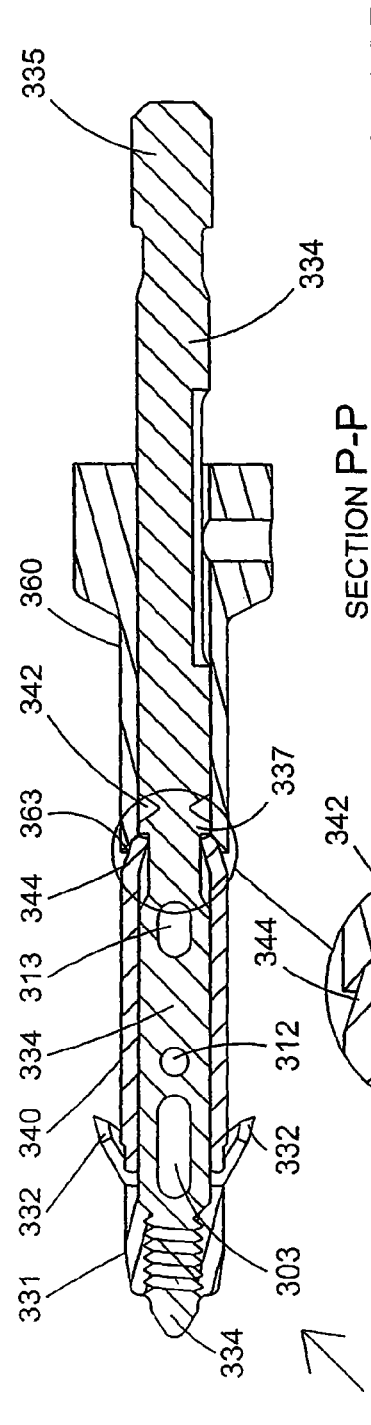
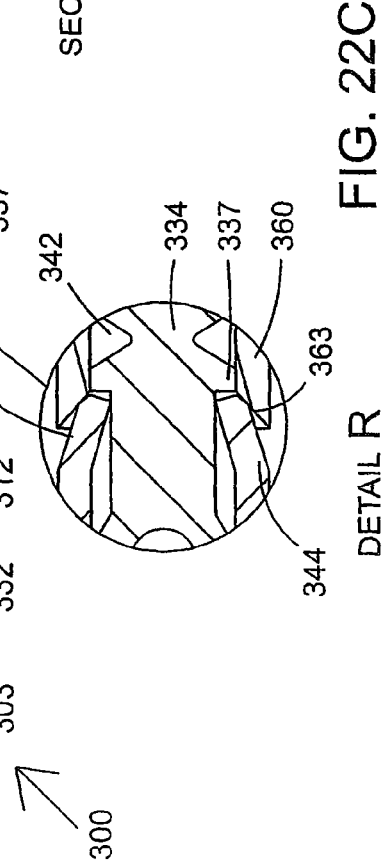
FIG. 22A
FIG. 22B
SECTION P-P
FIG. 22C
DETAIL R

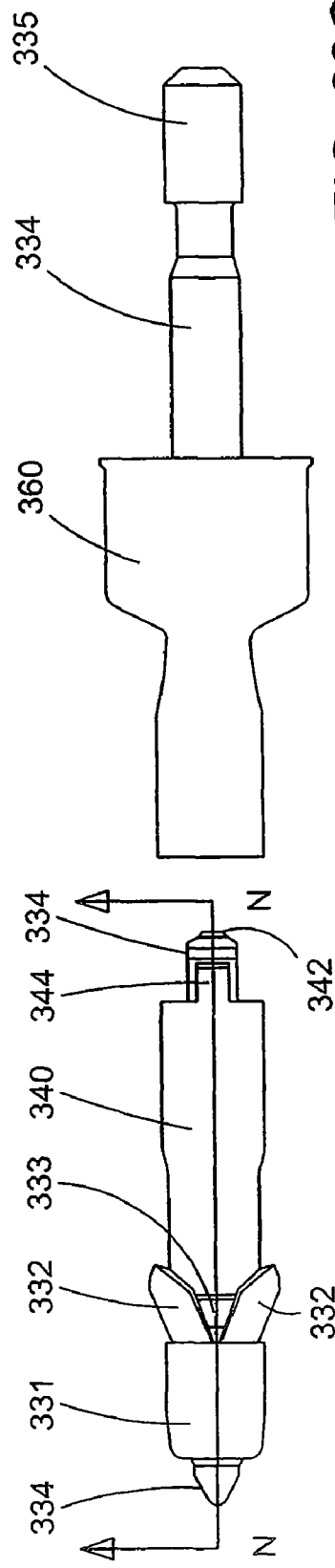
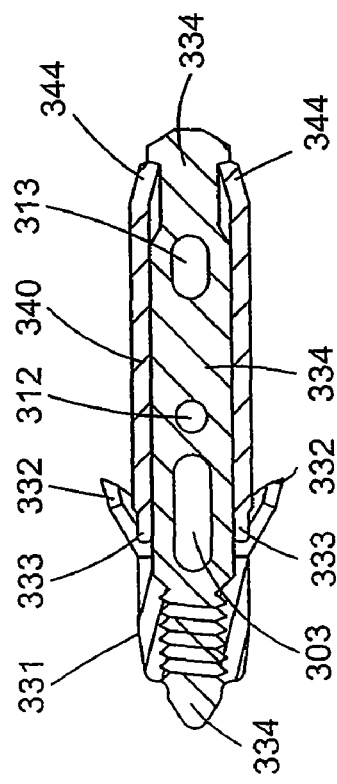
FIG. 23C
FIG. 23D

KNOTLESS SUTURE ANCHOR AND METHOD FOR KNOTLESSLY SECURING TISSUES

CROSS REFERENCE TO RELATED APPLICATIONS

This is a divisional of U.S. patent application Ser. No. 10/661,135, filed Sep. 11, 2003 now U.S. Pat. No. 7,662,171 in the name of Hugh Sloan West Jr., and entitled "KNOTLESS SUTURE ANCHOR AND METHOD FOR KNOTLESSLY SECURING TISSUE", which is a divisional of U.S. patent application Ser. No. 09/995,288, filed Nov. 26, 2001 now U.S. Pat. No. 6,692,516 in the name of Hugh S. West, Jr., and entitled "KNOTLESS SUTURE ANCHOR AND METHOD FOR KNOTLESSLY SECURING TISSUE", which application claims the benefit and priority of U.S. Provisional Application No. 60/253,534 filed Nov. 28, 2000 entitled "Arthroscopic Bankart Repair With Suture Anchor Without Tying Knot", the disclosures of which are incorporated by reference herein in their entirety.

BACKGROUND OF THE INVENTION

The present invention relates to suture or surgical anchors and methods for installing same in tissue. In particular, the present invention relates to a suture anchor for anchoring a second tissue such as soft tissue to a first tissue such as bone without requiring the tying of a knot in the suture which attaches the second tissue to the first tissue. In situations where ligaments or other soft tissue are being sutured to bone, a suture anchor is commonly employed. The anchor is inserted into a borehole in the bone and a suture extending from the anchor is attached to the soft tissue to be secured to the bone. A knot must then be made in the suture. Alternatively, the suture may be attached to the tissue prior to insertion of the anchor into the bone borehole. In this case also, a knot must be made in the suture to tie the tissue to the anchor. Often, due to tight clearances, particularly in arthroscopic surgery, it is difficult to manipulate the sutures to tie the knot. The present invention relates to a method and device using a suture anchor to attach soft tissue to bone or other tissue which allows the soft tissue to be secured without tying a knot.

The present invention may use modified forms of anchors such as the Mini Mite™ or Ultrafix® anchors of Linvatec Corporation of Largo, Fla.

As described above, a problem with many known suture anchors is that the sutures must be tied to the soft tissue to be secured to the bone. This entails tying knots in the sutures after they have been threaded through the soft tissue. It would be advantageous to provide a suture anchor and method wherein the need to tie suture knots is eliminated. There is a need for a suture anchor which eliminates the need to tie a knot in the suture to secure the suture to the soft tissue and thus the soft tissue to the bone.

Although the above discussion has been made in the context of securing soft tissue to bone tissue, the invention is equally applicable to the securement of various type tissues to each other and also to securement of prosthetic and/or man-made or replacement tissues to other tissue.

A number of patents which eliminate knotting of sutures are known. For example, U.S. Pat. No. 6,200,329 to Fung et al. shows a suture collet. This reference shows a device which takes the place of a knot. However, it does not teach or suggest a suture anchor which can be used to attach soft tissue to bone tissue without tying a knot.

U.S. Pat. No. 5,902,321 to Caspari et al. shows a connector wherein a suture is secured between an outer and an inner member. Similar to Fung et al., Caspari et al. shows a suture securing device which replaces a knot.

Another reference is U.S. Pat. No. 4,750,492 to Jacobs which shows a suture clamping device which replaces a knot.

None of these references show a suture anchoring device which provides a knotless means to secure soft tissue to the suture anchor and thus to the tissue into which the suture anchor is installed. Further, although these devices show knotless suture clamping means, the use of these devices themselves is cumbersome and often presents the same problems encountered in tying a suture knot, particularly in arthroscopic applications.

Other known patents include U.S. Pat. Nos. 5,948,000 and 5,948,001 to Larson. These patents show a suture anchor in which the suture is disposed between a setting pin and a socket. However, there is no suggestion of a knotless securement of the suture to the tissue to be attached to the suture anchor in these references.

Another suture anchor is shown in McDevitt, U.S. Pat. No. 5,814,071. In this device the suture is tied to a suture retainer of the suture anchor but there is no teaching or suggestion of knotless securement of tissue to be attached to the suture anchor.

Steiner, U.S. Pat. No. 6,221,107, shows a device for ligament fixation in which ligament strands are held by a clamping action. However, this reference does not teach or suggest a knotless securement of a suture to a suture anchor.

U.S. Pat. No. 6,156,039 to Thal shows knotless suture securement using a snagging member in which a snagger recess snags a snagger stopper means prior to insertion of the anchor into the bone mass thereby to secure tissue to the bone mass. U.S. Pat. No. 6,143,017 to Thal is similar. U.S. Pat. No. 6,045,574 to Thal shows a snagging anchor which is received in a hollow anchoring means thereby to allow tissue to be secured to other tissue. Although these patents show knotless securement of the suture back on the anchor itself, they provide a very cumbersome means for securing the suture to the anchor. After the suture has been threaded through the tissue to be attached to the bone, it must be snagged by the snagging member, which is often difficult to do, particularly in the tight confines of arthroscopic surgery.

U.S. Pat. Nos. 6,149,669, 6,129,762, 6,022,373, 5,843,127, 5,645,589, 5,690,649 and 5,741,300 show various patents of Lehmann K. Li which are exemplary of suture anchors of the type which may be employed by modifying them for use with the present invention. However, none of those references teach or suggest a suture anchor employing a means for knotlessly securing the soft tissue to the tissue in which the anchor is secured. U.S. Pat. No. 6,149,669 shows a type of "button anchor" which utilizes a button or washer member secured to the anchor by suture to hold tissue in place. It also shows spanning sutures connected to plural suture anchors to secure tissue to bone. However, the requirement of a button/washer member or plural anchors may preclude these devices from a number of applications.

Accordingly, there is a need for a suture anchor which allows a first tissue to be knotlessly secured to the suture anchor thereby to secure the first tissue to second tissue in which the suture anchor is installed.

SUMMARY OF THE INVENTION

It is, accordingly, an object of the present invention to provide a suture anchor which allows tissue to be secured to tissue in which the anchor is installed without requiring tying of a knot.

It is furthermore an object of the present invention to provide a method for knotless securement of tissue to tissue in which a suture anchor is installed.

It is furthermore an object of the present invention to provide such a knotless suture anchor that is suitable for arthroscopic use.

It is yet still a further object of the present invention to provide a suture anchor which is relatively simple to install and which avoids the disadvantages of known anchors which require that sutures be knotted to secure the tissue or otherwise require that some form of clamping device be installed on the suture to secure the tissue to the suture anchor.

It is furthermore an object of the invention to provide a suture anchor that, in one operation, and without tying a knot in the suture, secures the suture anchor into the suture anchor receiving tissue and secures a tissue to be attached or reattached to the anchor, thereby securing both tissues together.

The above and other of the present invention are achieved by a suture anchor comprising: a deformable portion for engaging with a wall of a borehole in a first tissue member, a shaft for providing a force to the deformable portion to deform the deformable portion to cause the deformable portion to engage the wall of the borehole, a suture retaining portion in at least one of the deformable portion and the shaft for retaining two suture portions in the retaining portion with a loop formed between the two suture portions, the loop adapted to traverse a second tissue member to be attached to the first tissue member; and wherein application of the force to deform the deformable portion causes engagement of the deformable portion with the borehole to secure the suture anchor to the first tissue and clamping of at least one of the two suture portions in the suture retaining portion thereby to secure the suture forming the loop in the suture retaining portion and secure the second tissue to the suture anchor.

The objects of the invention are also achieved by a suture anchor comprising a deformable portion for engaging with a wall of a borehole in a first tissue member, a shaft for providing a force to the deformable portion to deform the deformable portion to cause the deformable portion to engage the wall of the borehole, a first suture retaining portion in at least one of the deformable portion and the shaft for retaining a first suture portion, a second suture retaining portion in at least one of the deformable portion and the shaft for retaining a second suture portion, whereby a loop is formed in a suture between the first and second suture portions, the loop adapted to traverse a second tissue member to be attached to the first tissue member, the first suture retaining portion comprising a first retaining portion wherein the first suture portion comprising an end of the suture is fixedly secured to the anchor; and wherein application of the force to deform the deformable portion causes engagement of the deformable portion with the borehole to secure the suture anchor to the first tissue and clamping of the second suture portion in the second suture retaining portion thereby to secure the suture forming the loop between the first and second suture retaining portions and secure the second tissue to the suture anchor.

The objects of the invention are furthermore achieved by a method for securing first and second tissues with a suture anchor comprising the steps of forming a borehole in the first tissue, threading a suture through the second tissue forming a loop in the suture with the tissue thereby secured in the loop, the loop defining two suture portions; attaching the two suture portions to the anchor whereby at least one of the two suture portions is threaded through the anchor and initially movable with respect to the anchor, and providing a force to a shaft of the anchor, the force causing clamping of the at least one of the two suture portions in the anchor and deformation of a deformable portion of the anchor to cause the deformable portion to engage a wall of the borehole thereby to secure the suture anchor in the first tissue and the loop holding the second tissue to the suture anchor.

Other objects, features and advantages of the present invention will become apparent from the following detailed description:

BRIEF DESCRIPTION OF THE DRAWINGS

The invention will now be described in greater detail in the following detailed description with reference to the drawings in which:

FIG. 16 is a further view of the suture anchor in its deployed state after fracturing at a frangible connection, the part not shown that fractures away being discarded;

FIG. 20A is a phantom view of the third embodiment of the suture anchor in its deployed state;

FIG. 20B shows the suture anchor of FIG. 20A in its deployed state along line H-H of FIG. 20A;

FIG. 22A shows a slightly modified version of the deployed suture anchor according to the third embodiment prior to rupture of a frangible connection of the suture anchor holding a discardable portion to the portion shown in FIG. 21A;

FIG. 22B shows the suture anchor of FIG. 22A along lines P-P of FIG. 22A;

FIG. 22C shows a detail of the suture anchor of FIGS. 22A and 22B;

FIG. 23C is a plan view of the suture anchor of FIG. 23B; and

FIG. 23D is a sectional view of the suture anchor or FIG. 23C taken along lines N-N.

DETAILED DESCRIPTION OF EMBODIMENTS OF THE INVENTION

Figure 1:
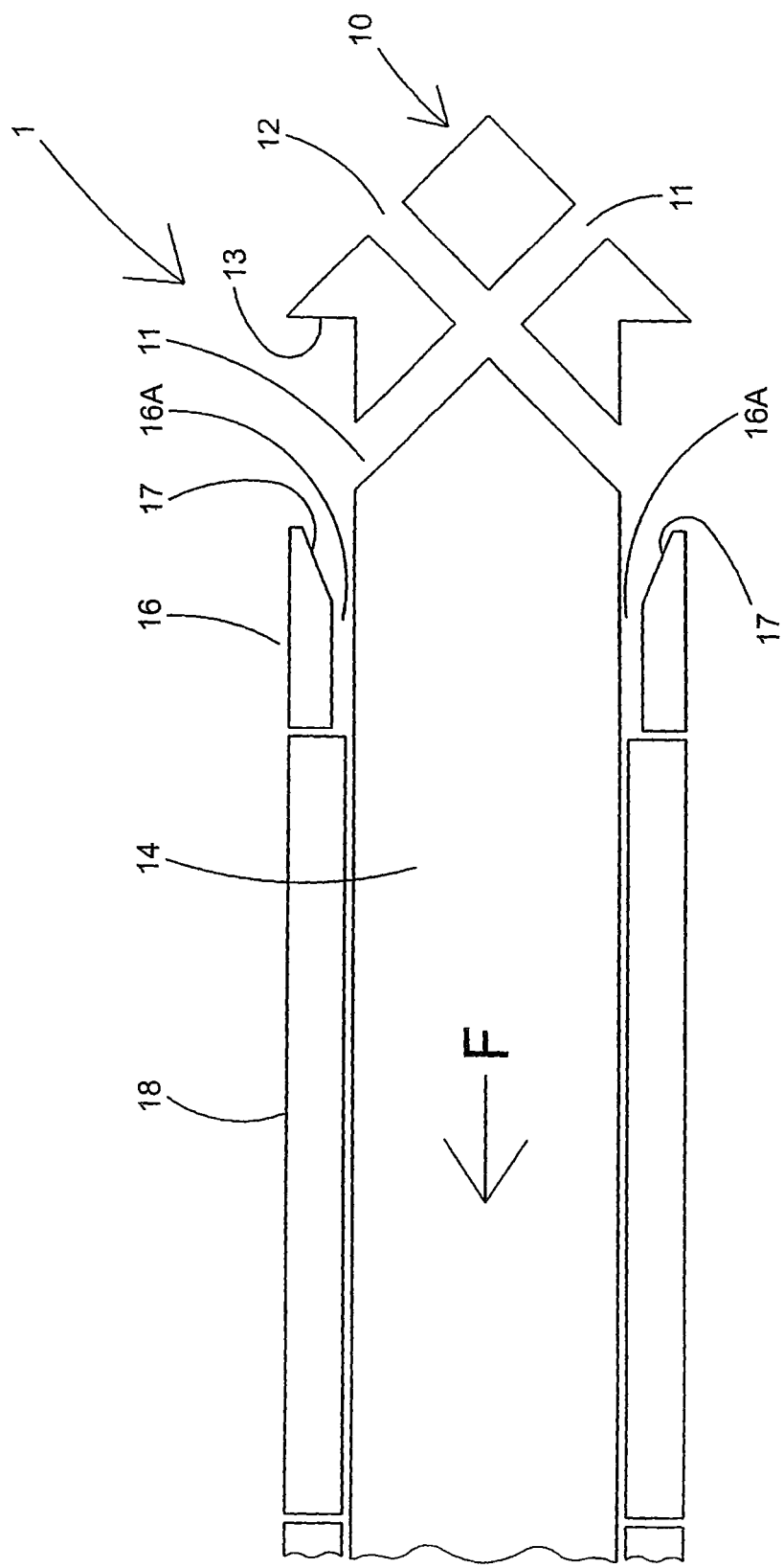
FIG. 1 shows a schematic representation of one embodiment of a suture anchor accomplishing knotless suturing according to the present invention.

Turning now to FIGS. 1 to 10, a first embodiment and method according to the present invention is disclosed. This first embodiment of the suture anchor may be made by modifying a suitable suture anchor such as the Ultrafix® surgical anchor available from Linvatec Corporation. The general configuration of this anchor is shown, for example, in U.S. Pat. Nos. 6,129,762 and 5,843,127, assigned to the assignee hereof and incorporated by reference herein. FIG. 1 shows the modified anchor schematically in cross section, the anchor being generally indicated by reference numeral 1 and including a conical head portion 10 having intersecting holes 11 and 12 drilled therethrough at an angle, a shaft 14 connected to the head 10, a cylindrical suture clamping section 16 with chamfered internal distal edge 17 and a crown portion 18. The crown portion 18 is shown schematically, and includes opposed sets of radially extendable interdigitated fingers, not shown in detail, which penetrate into the tissue bore hole, for example, a bone borehole, upon axial movement of the shaft 14 in the direction F which causes the head 10 to move against the cylindrical section 16 and thence the crown portion 18 thereby forcing the fingers of the crown portion 18 radially outwardly into penetrating engagement with the borehole. The head 10 is provided with a shoulder 13 which transfers the axial force in the direction F to the clamping portion 16 and thence to crown portion 18.

The head 10 shown at the distal end of the shaft 14 is modified to include two intersecting obliquely drilled holes 11 and 12 entering opposing surfaces of the head. The two holes 11 and 12 exit proximally through the shaft 14 in proximity to the junction between the shaft and the conical head. These holes are sized to accommodate the suture.

The cylindrical suture clamping section 16 is disposed proximally with respect to the head. It is sized larger than the diameter of the shaft 14 to allow a press fit of the sutures between the shaft 14 and cylindrical portion 16, as will be explained in greater detail below. Additionally, at the internal distal edge, a chamfer 17 is provided to prevent damage to the clamped suture, also to be explained below.

The crown portion 18 is shown schematically but includes two opposed sets of fingers which are adapted, upon application of the force in direction F, to move radially outwardly, in known fashion, to penetrate into the borehole into which the anchor is inserted.

Figure 2:
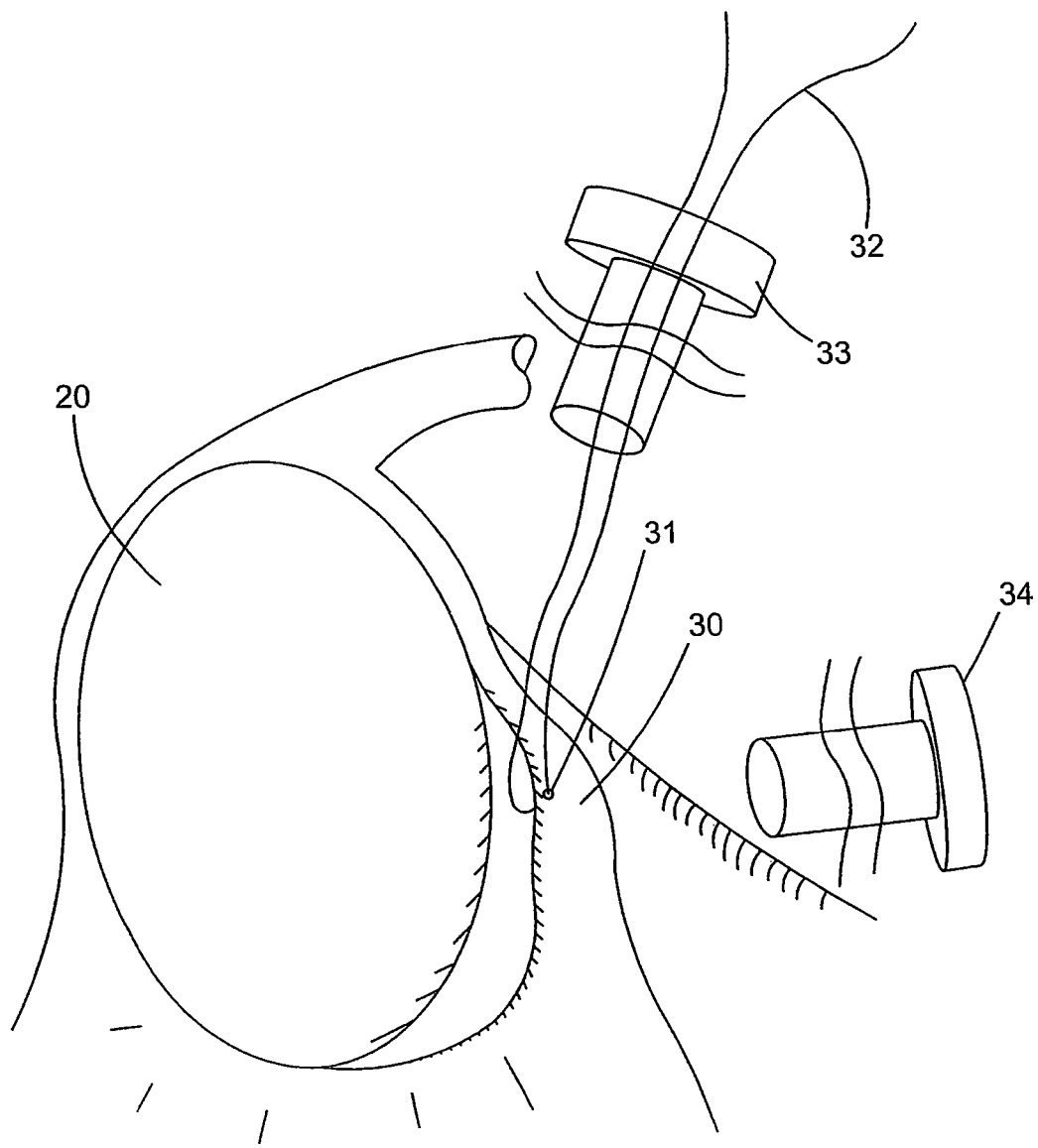
FIG. 2 shows a first step in a method for knotless suturing in accordance with the present invention using the example of the reattachment of a glenohumeral ligament to the glenoid.

Turning now to FIG. 2, this figure shows an example of how the suture anchor according to the invention can be used to knotlessly secure first and second tissues to each other, for example, bone portion 20 and soft tissue 30. In the illustrated embodiment, bone portion 20 represents the glenoid at the shoulder joint and the soft tissue 30, which has ruptured from the humerus 20, is the inferior glenohumeral ligament. As shown, the suture 32 is passed through the leading edge of the ligament, as shown at 31, under arthroscopic visualization. Any known technique can be used for threading the suture through the ligament such as a Caspari suture punch or suture hook. Suitable portals 33 and 34, known to those of skill in the art, are used to assist in the passage of sutures, anchors and tools used in the procedure.

Figure 3:
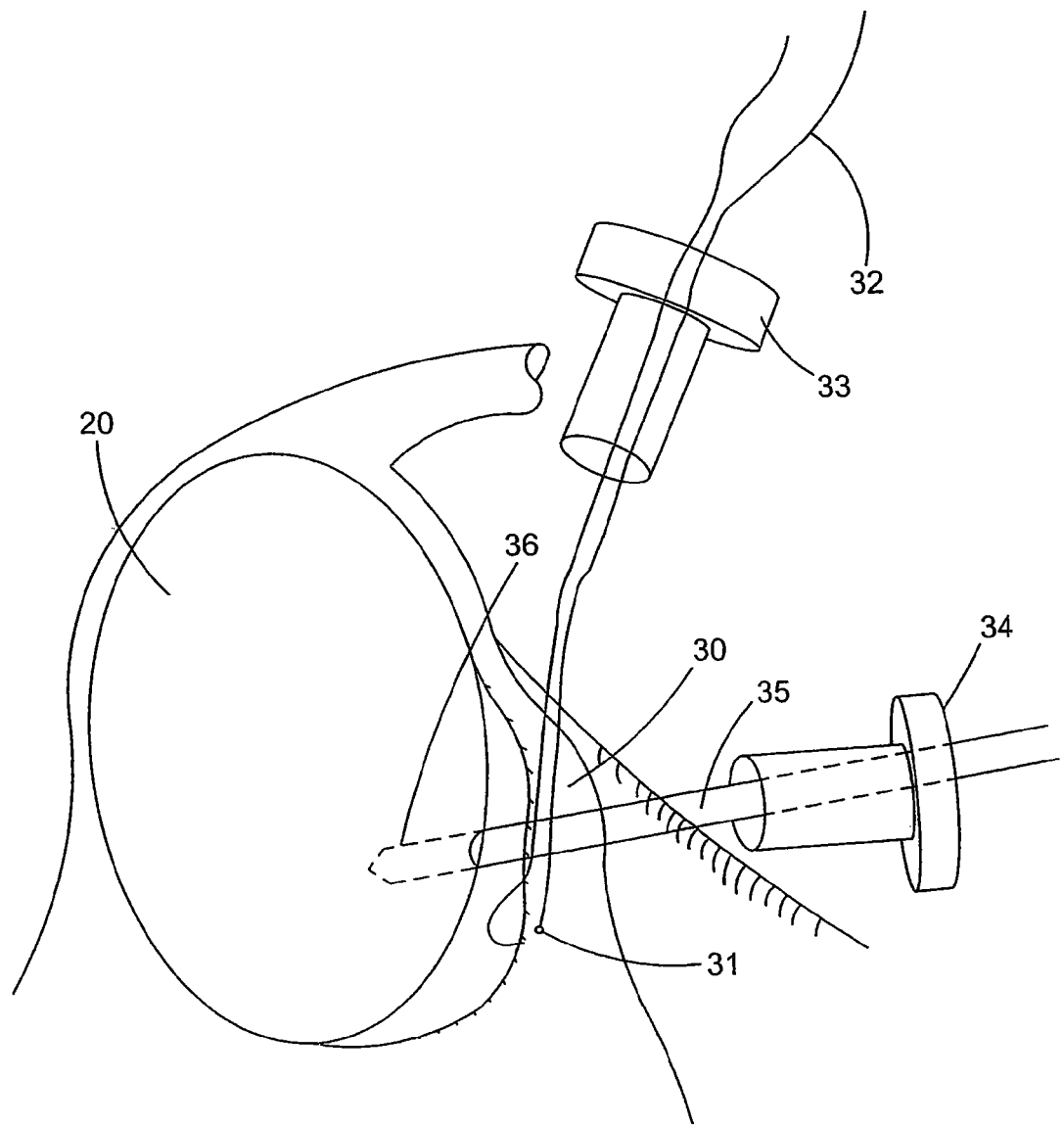
FIG. 3 shows a second step in the process described in FIG. 2 showing a step of drilling a borehole into the bone.
Figure 4:
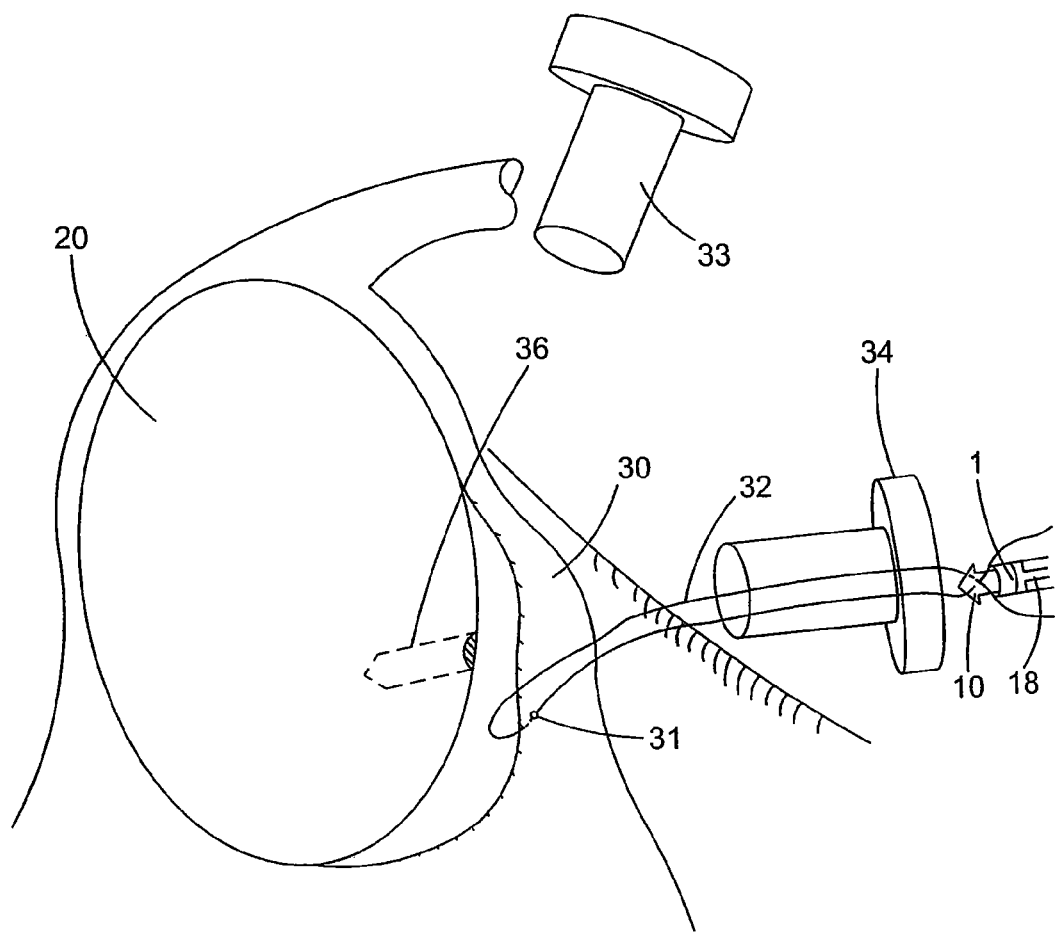
FIG. 4 shows a further step in the process including introducing the suture anchor threaded with the suture.

As shown in FIG. 3, a drill 35 is passed through the portal 34 and borehole 36 is prepared in the bone portion. As shown in FIG. 4, the ends of the suture 32 are withdrawn from portal 33 and now passed through the portal 34. The suture anchor 10 as shown in FIG. 1 is loaded onto the insertion tool, for example, a known insertion gun for this general type of anchor, and each of the two suture ends is threaded through the holes 11 and 12 of the distal tip of the anchor. The suture ends extend proximally out of the holes 11 and 12. An insertion tool of the general type used to deploy anchors of this general type is shown, for example, in U.S. Pat. No. 5,843,127.

Figure 5:
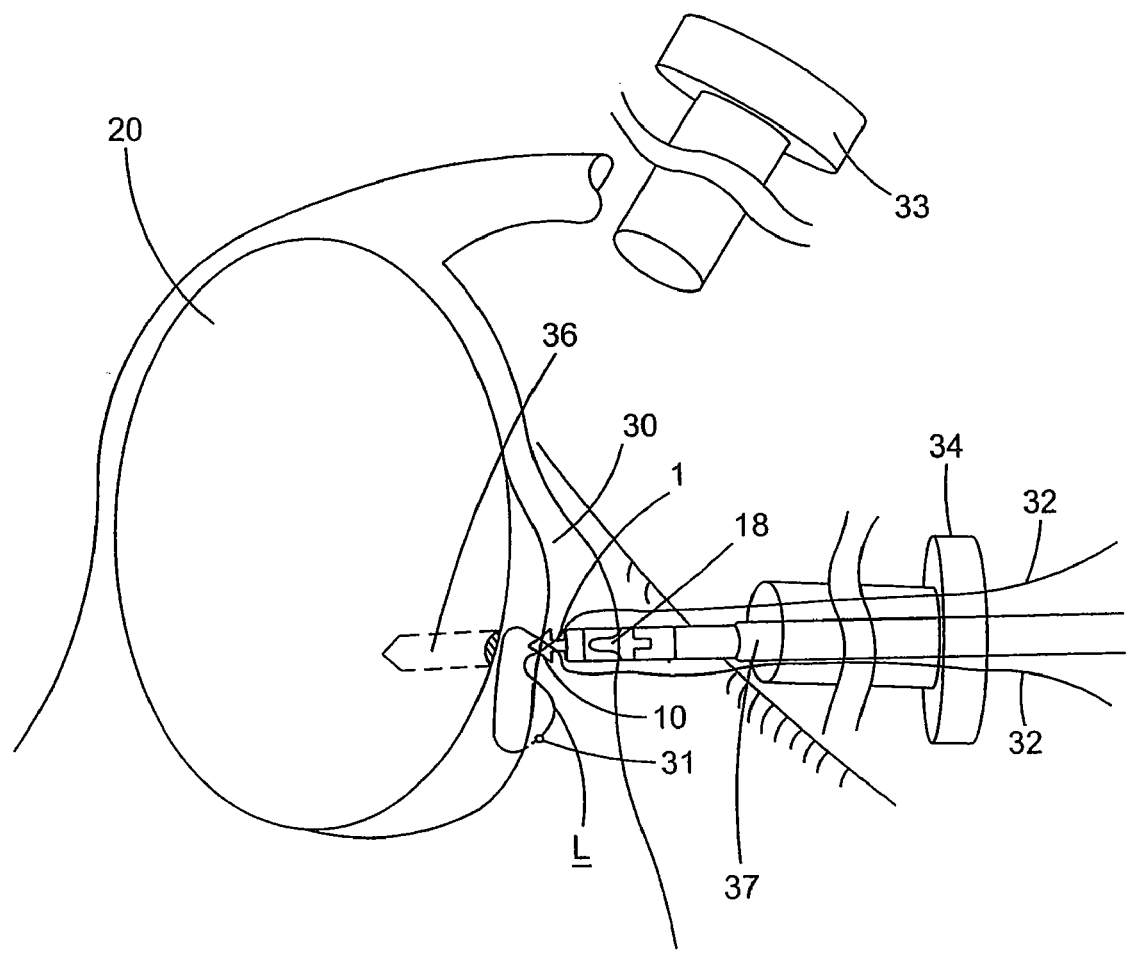
FIG. 5 shows still a further step in the process of introducing the suture anchor.
Figure 6:
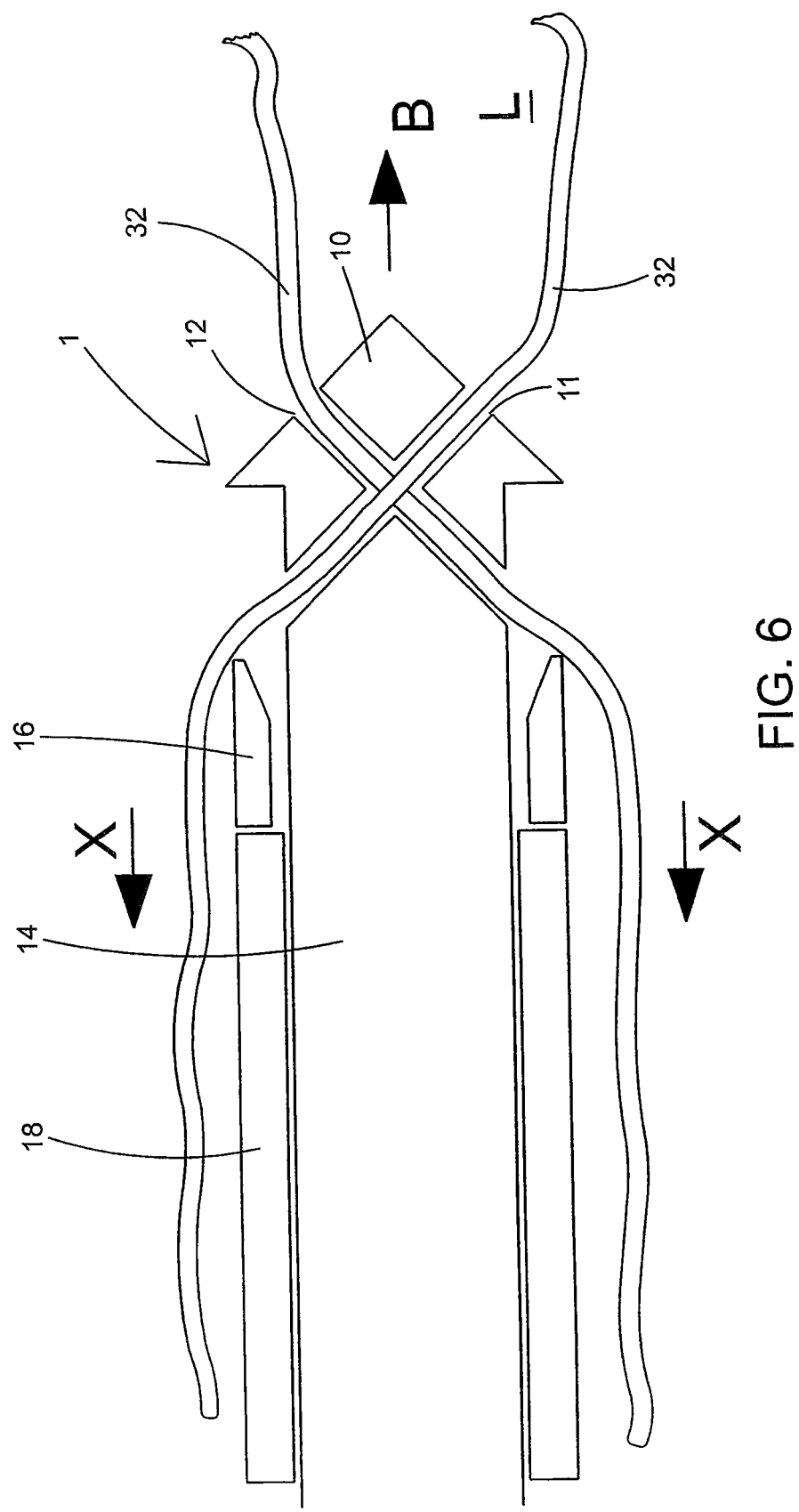
FIG. 6 is a schematic view of the suture anchor of FIG. 1 showing the suture threaded through the anchor according to one embodiment.
Figure 7:
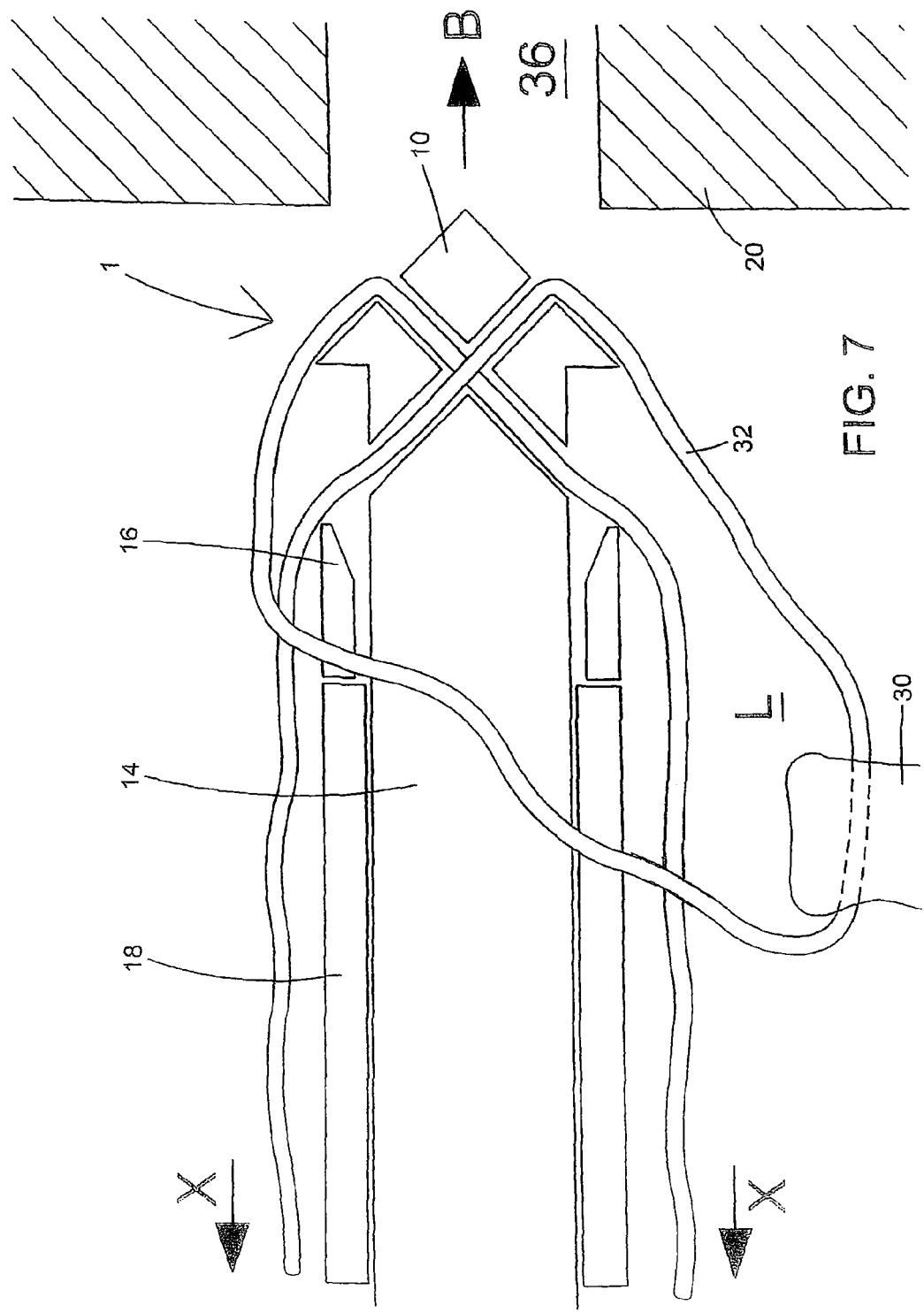
FIG. 7 shows the suture anchor of FIG. 1 as it is being inserted into the borehole in the bone with the suture attached to the tissue to be reattached.

As shown in FIG. 5, the suture is now drawn up through the holes 11 and 12 and the anchor 1 is advanced into the joint under arthroscopic visualization and into the borehole 36. The insertion tool distal end is shown at 37. FIG. 6 shows the direction of movement B of the suture anchor 1 into the borehole 36. Arrows X show how the free ends of the suture 32 are threaded through the holes 11 and 12. FIG. 7 shows the step of insertion of the anchor 1 into the borehole 36 with the tissue 30 secured to the thus formed loop L in the suture 32.

Figure 8:
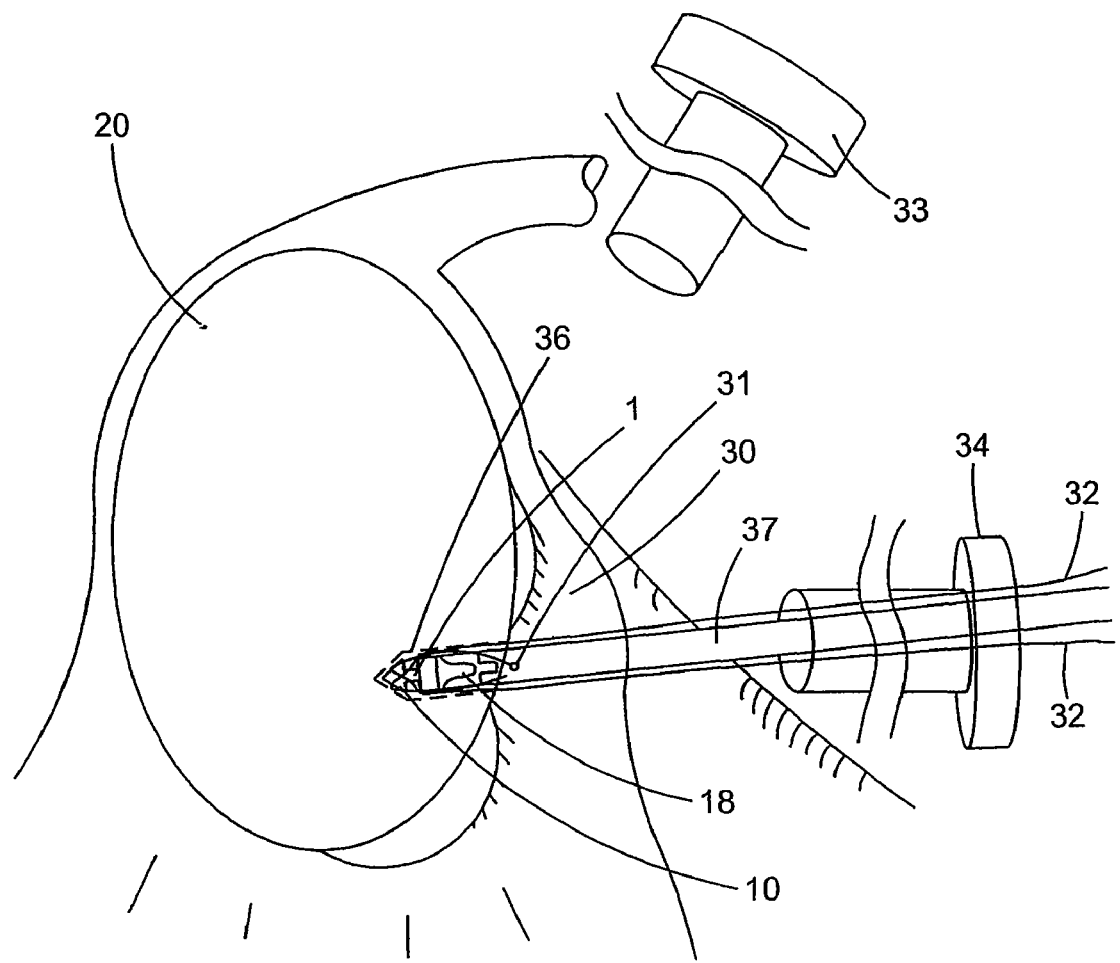
FIG. 8 shows the suture anchor inserted into the borehole with the tissue reattached prior to removal of the anchor insertion tool.

FIG. 8 shows the anchor 1 after insertion into the borehole 36 prior to deployment of the anchor. Tension is applied to the suture 32 free ends outside the joint to draw the tissue 30 snugly into proximity with the glenoid edge (see arrows X in FIGS. 6 and 7), directly over the suture anchor (see FIG. 8). The tension on the suture 32 can be provisionally evaluated at this point by traction/counter traction of the suture and insertion tool.

Figure 9:
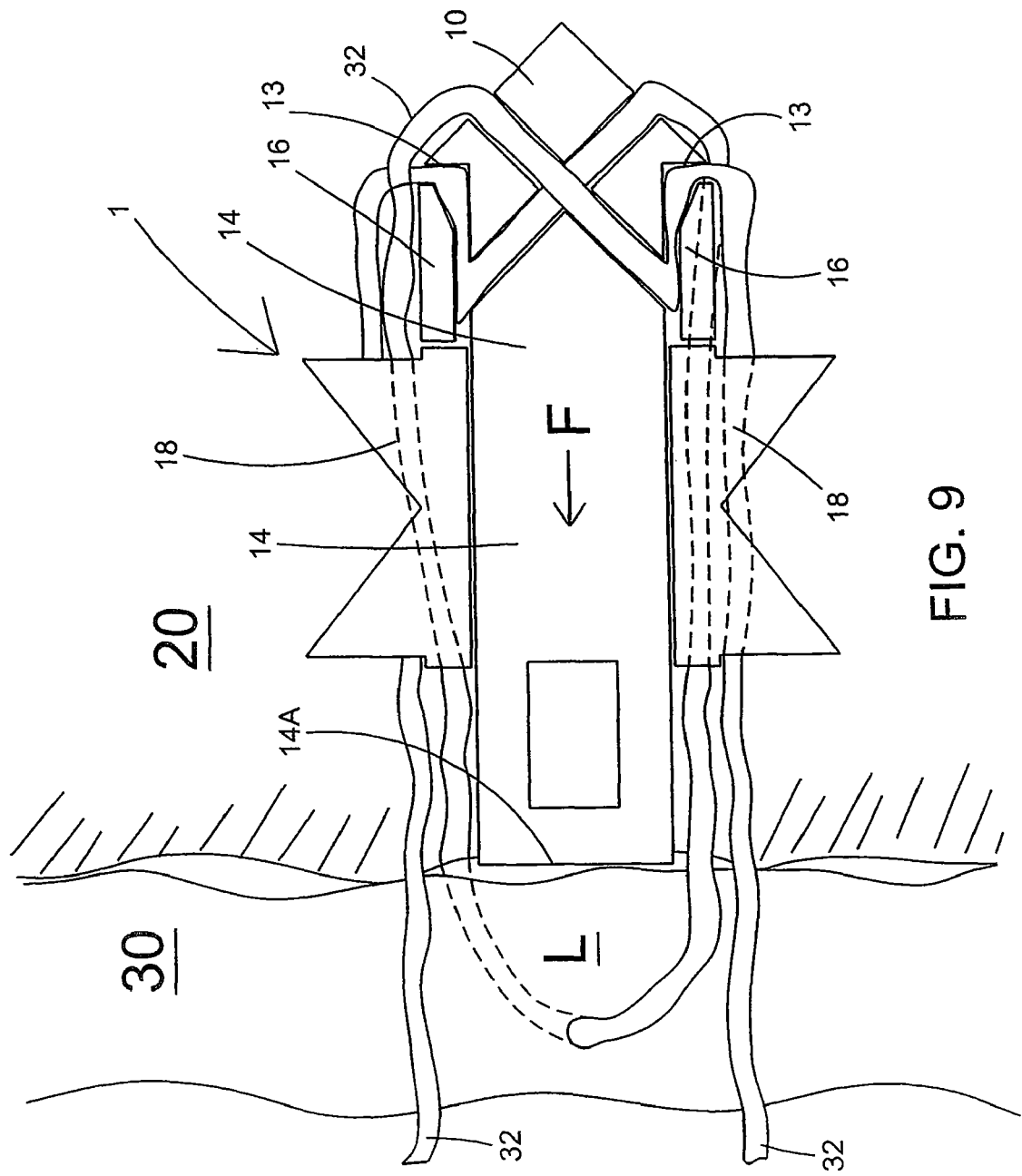
FIG. 9 shows the suture anchor inserted into the borehole fixedly holding the tissue to the bone.

FIG. 9 shows the anchor 1 after deployment of the fingers. As shown, by applying force in the direction F on the shaft 14, the head 10 is moved proximally toward the cylindrical clamping portion 16, causing the suture to be frictionally clamped into the space 16A (see FIG. 1) between the cylindrical portion 16 and the shaft 14 and between shoulder 13 and portion 16. As shown, the distal internal edge of the cylindrical portion 16 is gently chamfered at 17 to prevent damage to the suture as it is wedged between the cylindrical portion 16 and shaft 14 and between shoulder 13 and portion 16. The initial excursion of the insertion tool mechanism which causes the shaft 14 to move with respect to the cylindrical portion 16 and crown portion 18 locks the suture securely between the shaft portion 14 and portion 16. In addition, the convoluted path of the suture through holes 11 and 12 and in the space between clamping portion 16 and shaft 14, assists in locking the suture in place. The further excursion of the tool mechanism deforms the crown portion 18 and deploys the anchor in the bone. The free end of the suture exiting the margins of the borehole are clipped under arthroscopic visualization.

Figure 10:
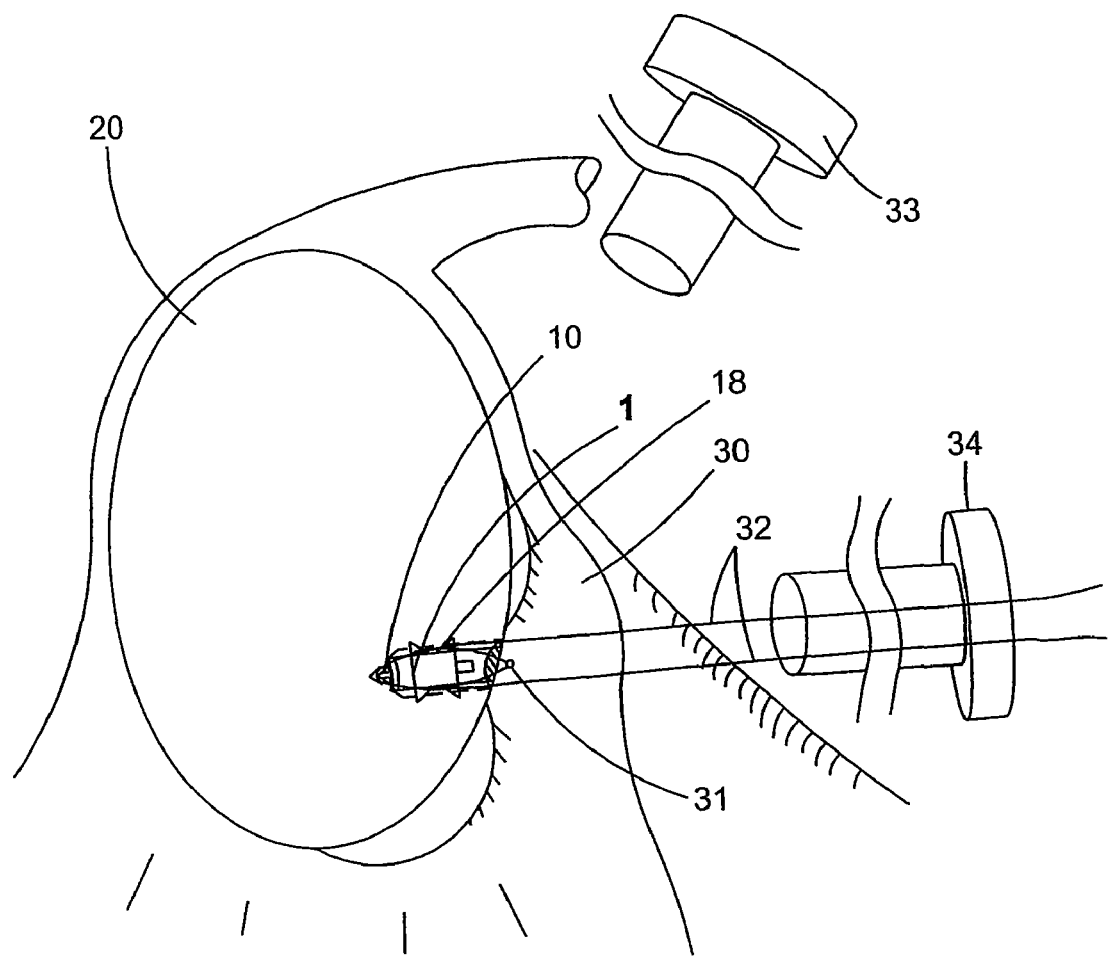
FIG. 10 shows the completed ligament repair.

A frangible or rupturable joint 14A in the shaft 1 can be employed, as well known, to separate the part of the anchor deployed in the tissue from a discarded portion of the anchor. FIG. 10 shows the completed repair prior to clipping the suture ends and withdrawing portals 33 and 34.

As shown, in the illustrated embodiment, the surgeon was not required to tie a knot in the suture extending from the anchor 1 in order to secure the tissue 30 to the anchor and hence to the tissue 20. The force applied to the shaft 14 by the insertion tool causes both the deployment of the anchor as well as securement of the tissue 30 to the tissue 20. This is a substantial advantage over suture anchors requiring knotting, eliminating a tedious, often cumbersome step, particularly in arthroscopic applications.

FIGS. 11A to 17 shows a second embodiment of a suture anchor according to the present invention. In contrast to the suture anchor shown in FIGS. 1-10, the crown portion of the suture anchor shown in this embodiment employs a single set of penetrating fingers extending only in the proximal direction instead of the interdigitated fingers shown in the embodiment of FIGS. 1-10. However, an anchor having interdigitated fingers of the type shown in FIG. 1 could also be used. Conversely, in the embodiment of FIGS. 1-10, a crown portion 18 having only a single set of proximally extending fingers can also be employed.

Figure 11A:
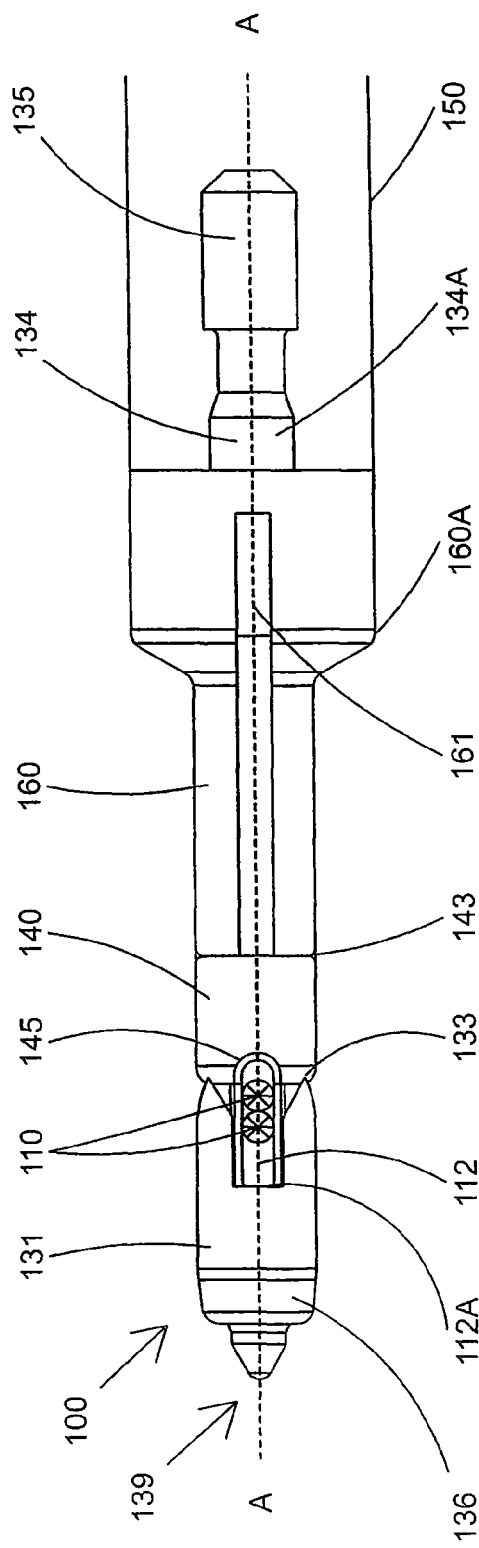
FIG. 11A shows a second embodiment of a knotless suture anchor in an undeployed state.
Figure 11C:
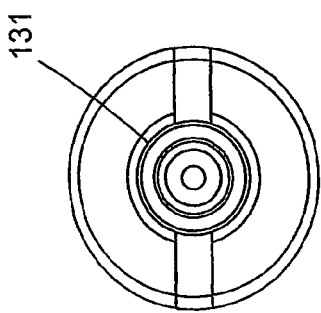
FIG. 11C is an end view of the suture anchor of FIG. 11A.

With reference now to FIG. 11, the anchor is generally shown at 100. The anchor includes a crown portion 131 with proximally extending fingers 132, a shaft 134 to which the crown portion 131 is secured, for example, by threads 131A, a first outer cylindrical portion 140 having a distal cam surface 133 and a second outer cylindrical portion 160 which expands to a larger diameter at 160A. The larger diameter portion 160A forms a shoulder stop for insertion of the anchor in the tissue borehole. The shaft 134 is movable axially in cylinders 140 and 160 and has an end 135 engageable by an insertion/actuation tool, generally indicated at 150 and which is like the tool discussed with respect to the first embodiment and known. Near the distal end 139 where shaft 134 attaches to crown portion 131, shaft 134 has an elongated opening 112 through which suture 110 can be introduced, as explained herein. Shaft 134 includes a frangible portion 142 which is breakable upon provision of a predetermined axial force by tool 150. The frangible portion 142 may comprise a score line or portion of reduced thickness designed so that it will rupture upon application of a preset, axial tensile force by the installation tool to the shaft 134. This rupture will leave the anchor, as described below, deployed in the borehole. The portion of the shaft 134 to the right of the connection 142 (as seen in FIG. 11) and the outer portion 160 are discarded. The line 143 shows where portion 160 abuts portion 140. Portion 140 remains in the borehole of the tissue when the anchor is deployed and portion 160 separates from portion 140 when joint 142 ruptures.

A suture 110 is first passed through (as shown at 201) the soft tissue 200 which is to be attached or reattached to the other tissue, for example bone, not shown. The two free ends of the suture 110 are then threaded through the opening 112 in the surgical anchor using a suitable threading tool, not shown.

Figure 11B:
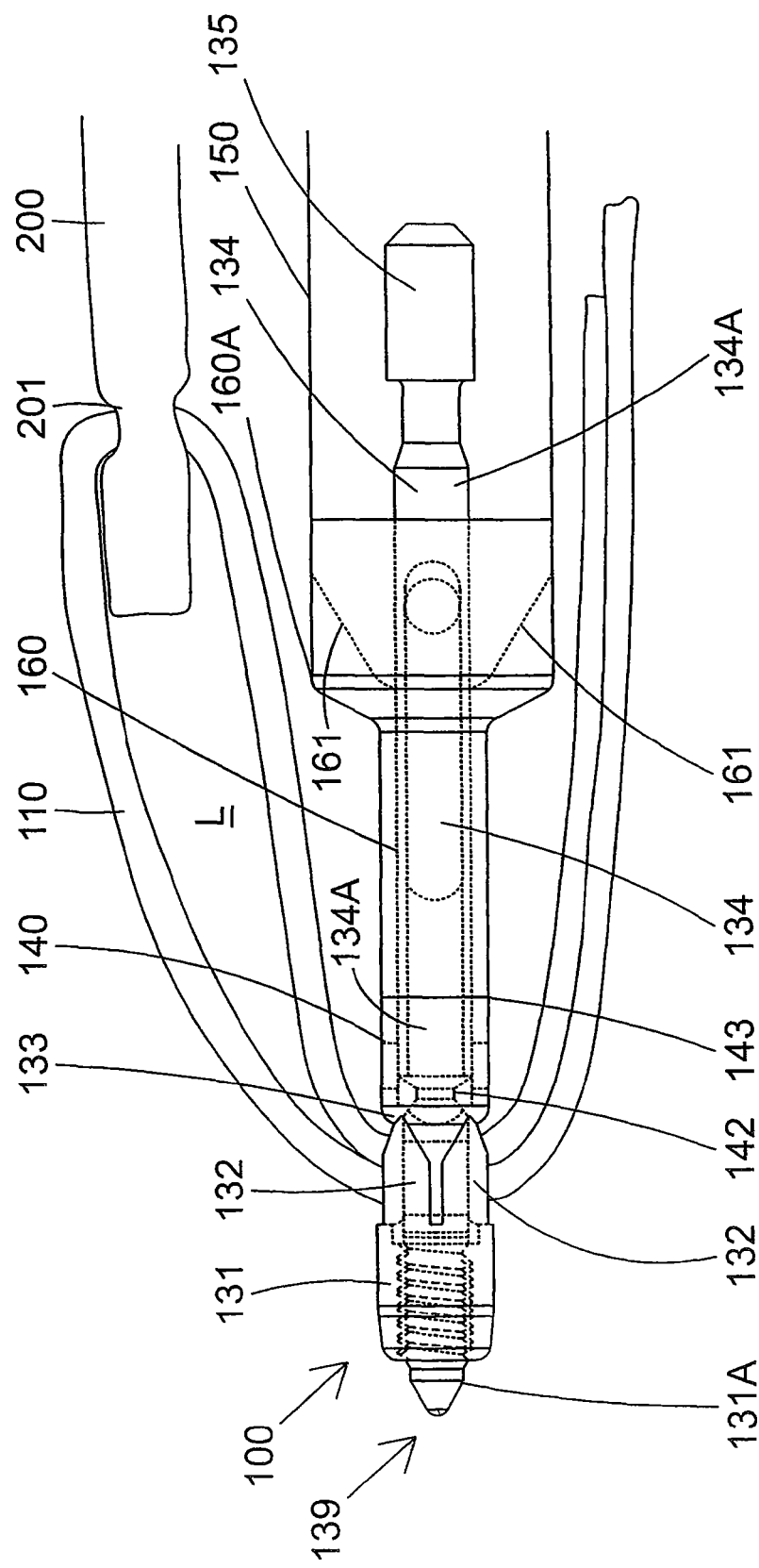
FIG. 11B shows the knotless suture anchor of FIG. 11A taken along the lines A-A of FIG. 11A.
Figure 12A:
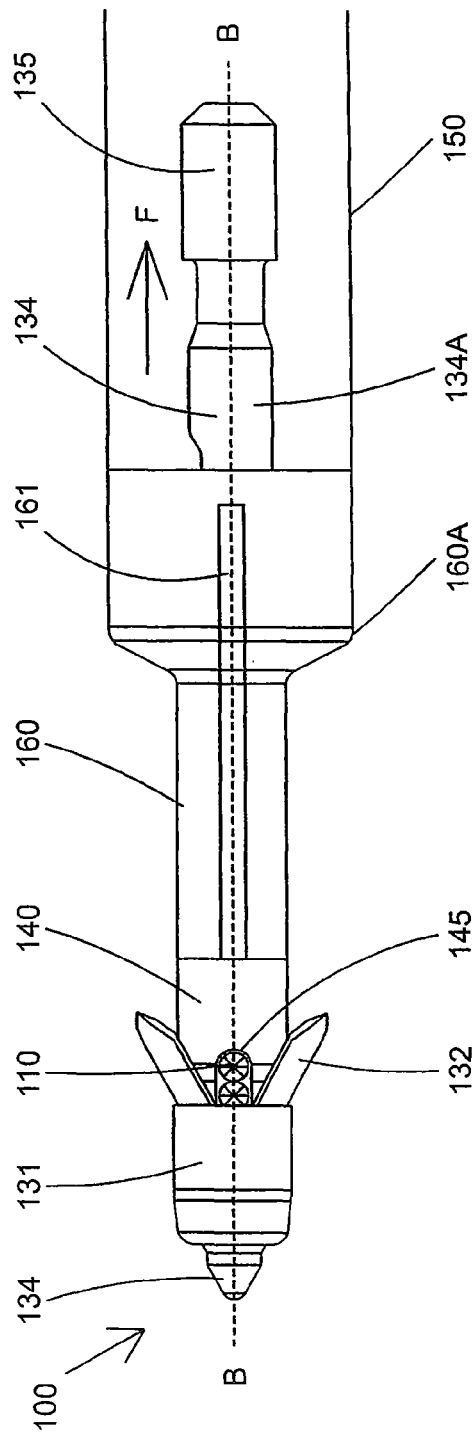
FIG. 12A shows the suture anchor of FIG. 11 after deployment.
Figure 12C:
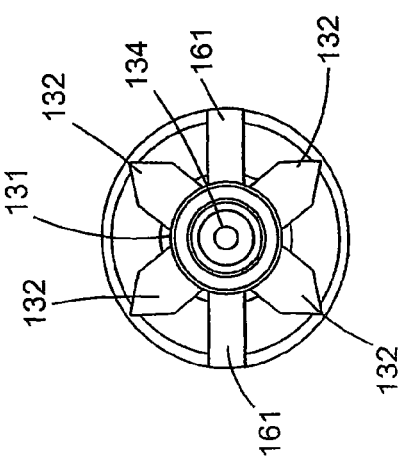
FIG. 12C is an end view of the suture anchor of FIG. 12A.
Figure 12B:
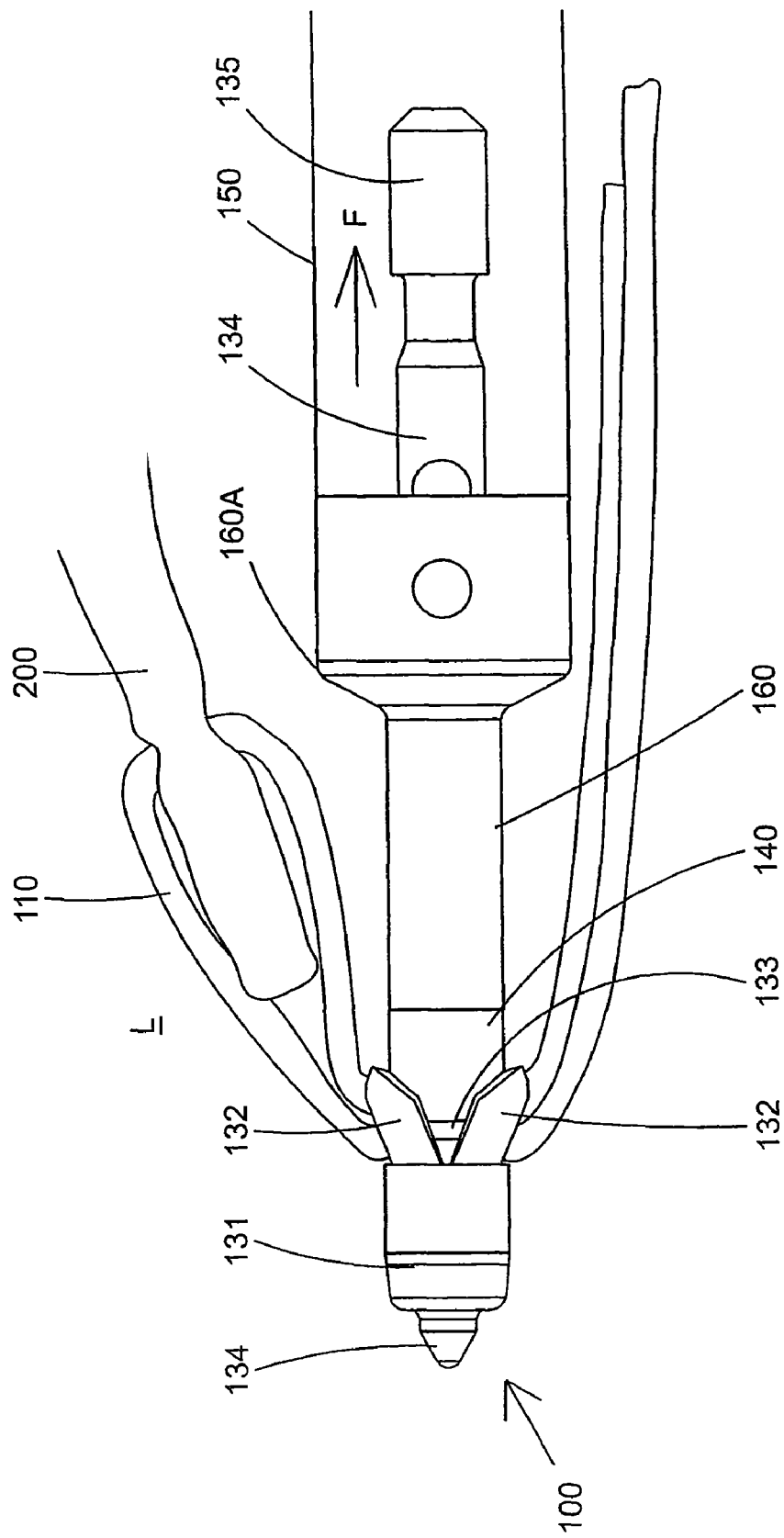
FIG. 12B shows the suture anchor of FIG. 12A attached to tissue taken along line B-B of FIG. 12A.
Figure 13:
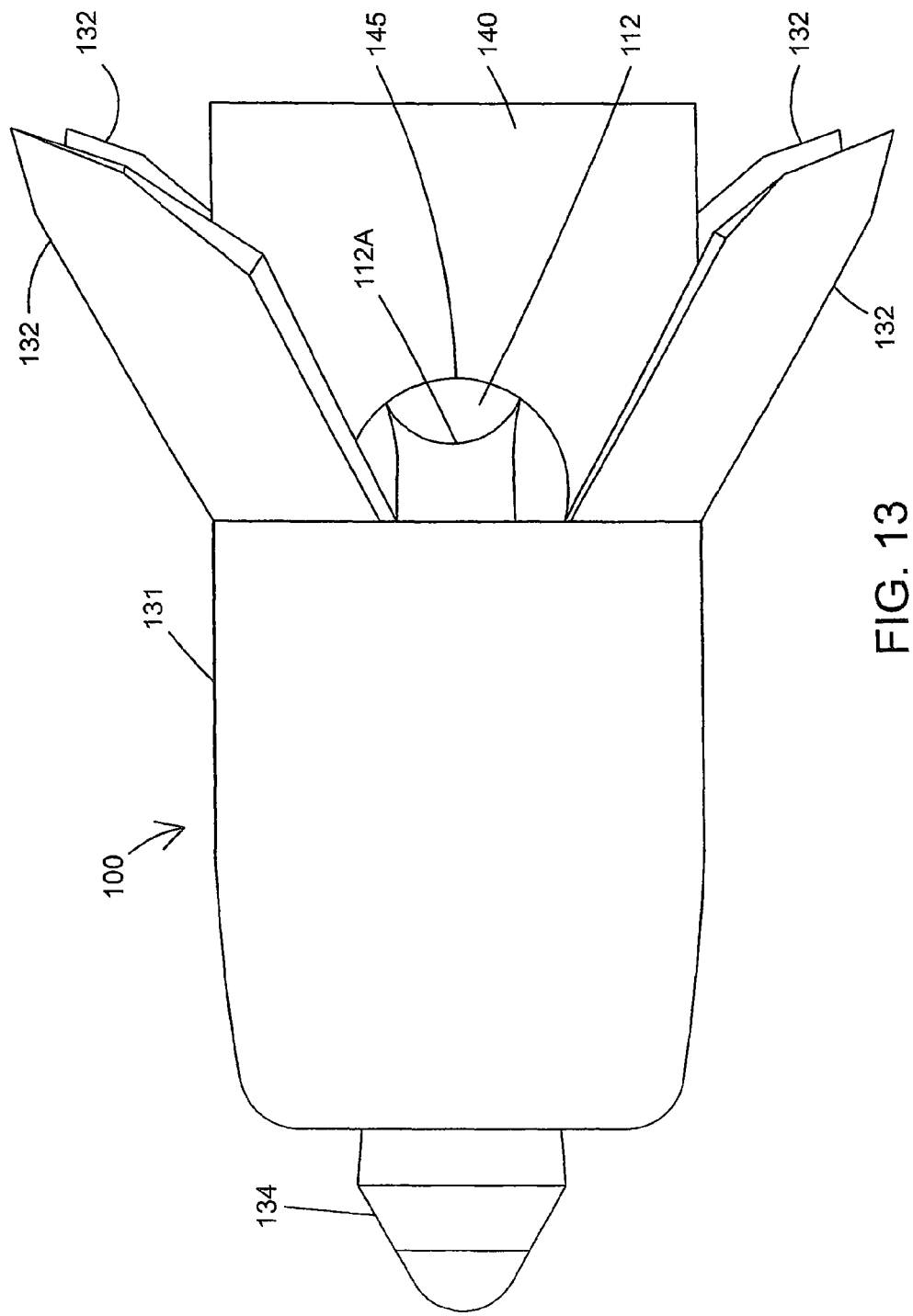
FIG. 13 is a closeup view of the suture anchor in its deployed state.
Figure 14A:
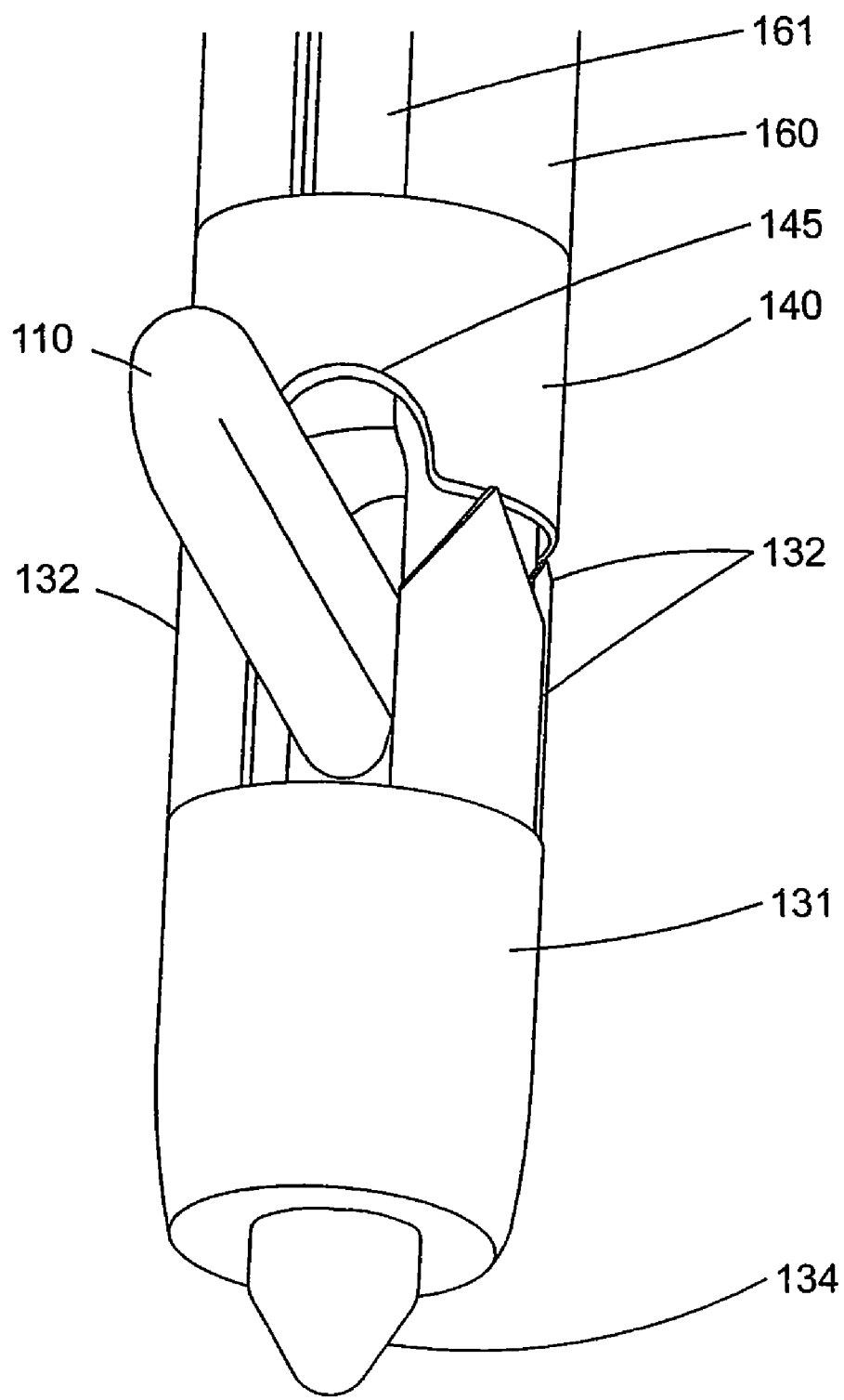
FIG. 14A shows a detailed view of the suture anchor in its undeployed state without showing the suture attached to any tissue.
Figure 14B:
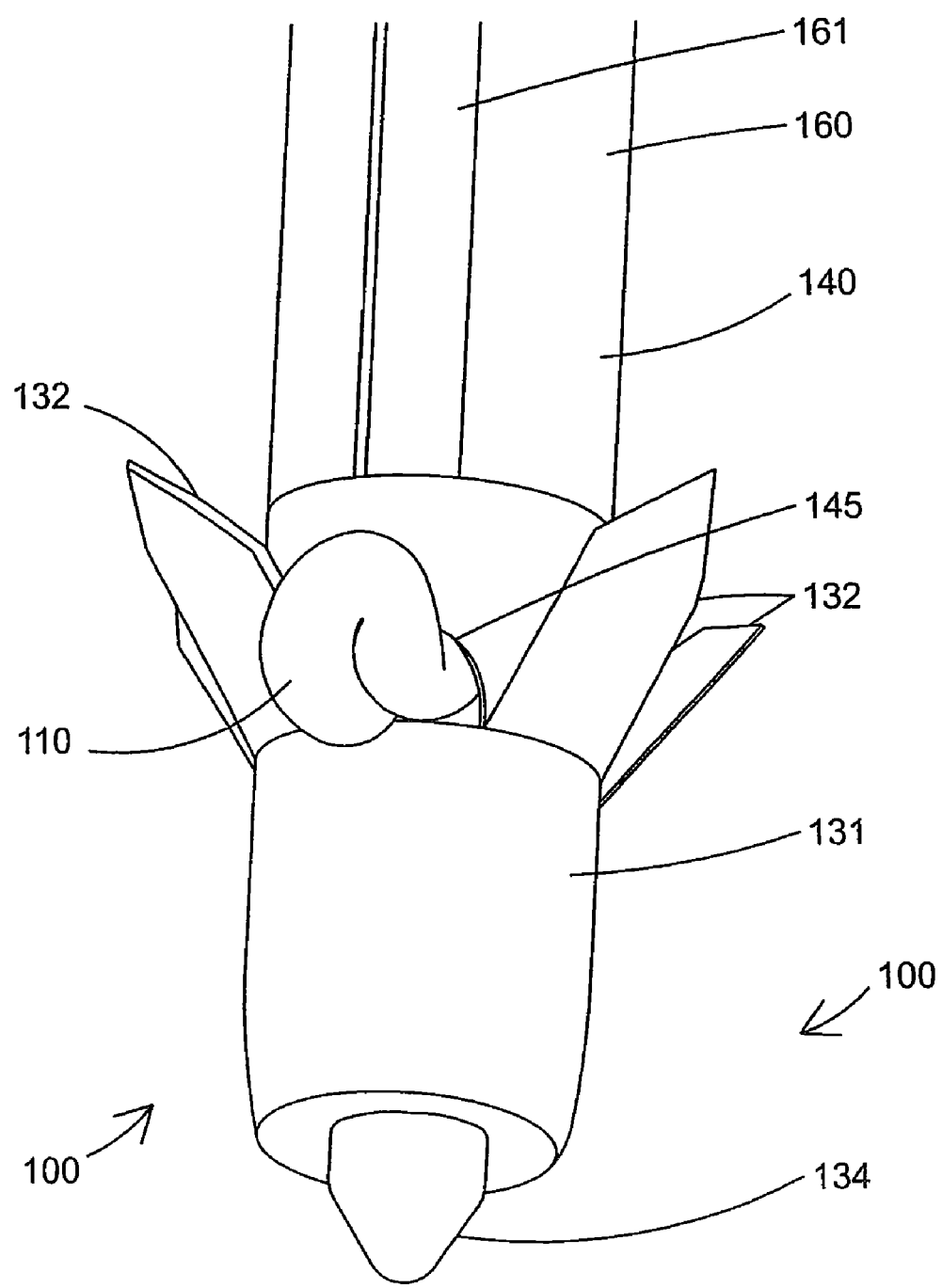
FIG. 14B is a closeup detailed view of the suture anchor according to the second embodiment in its deployed state without showing the suture anchor attached to tissue.
Figure 15A:
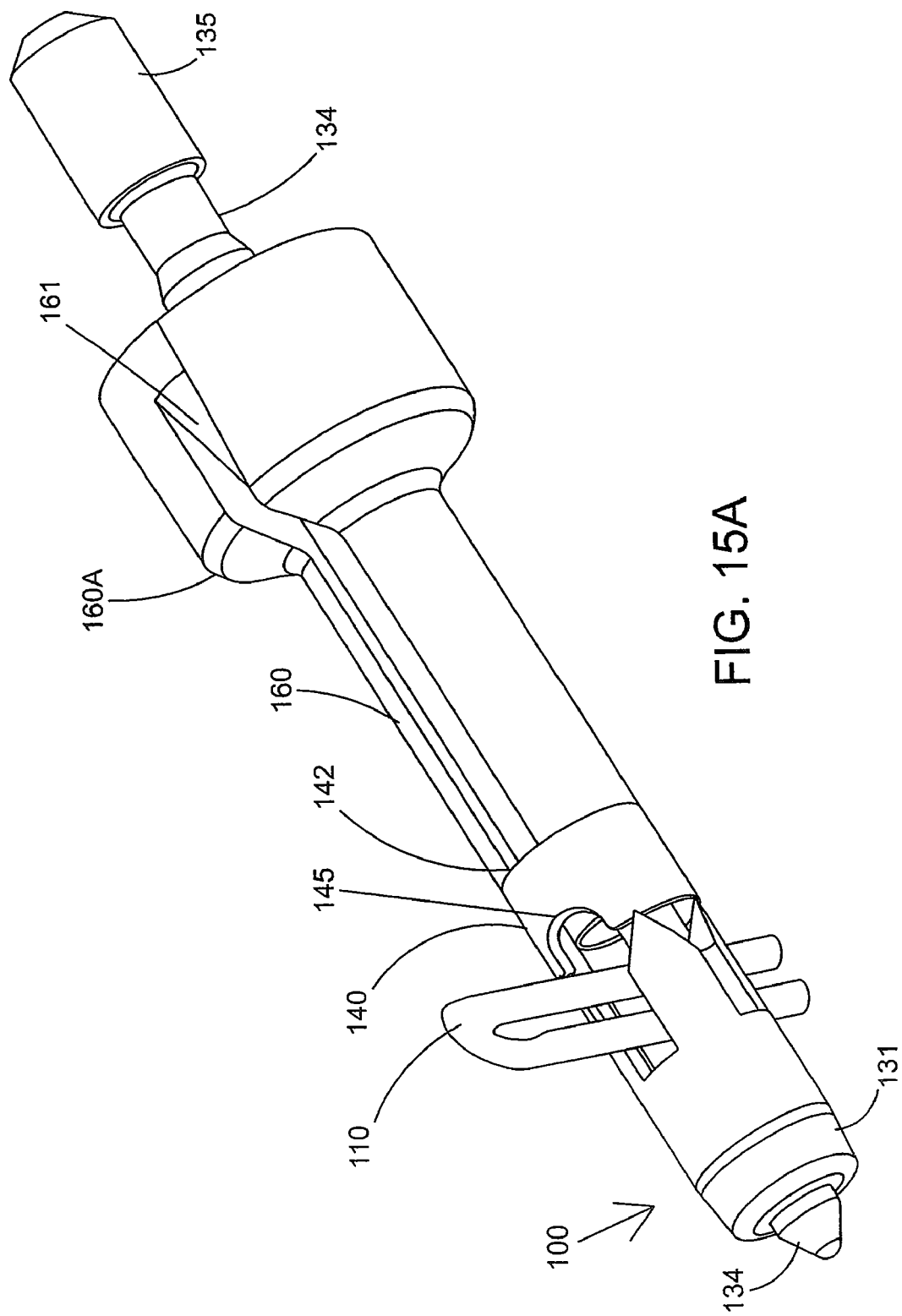
FIG. 15A is a perspective view showing the suture anchor in its undeployed state.
Figure 15B:
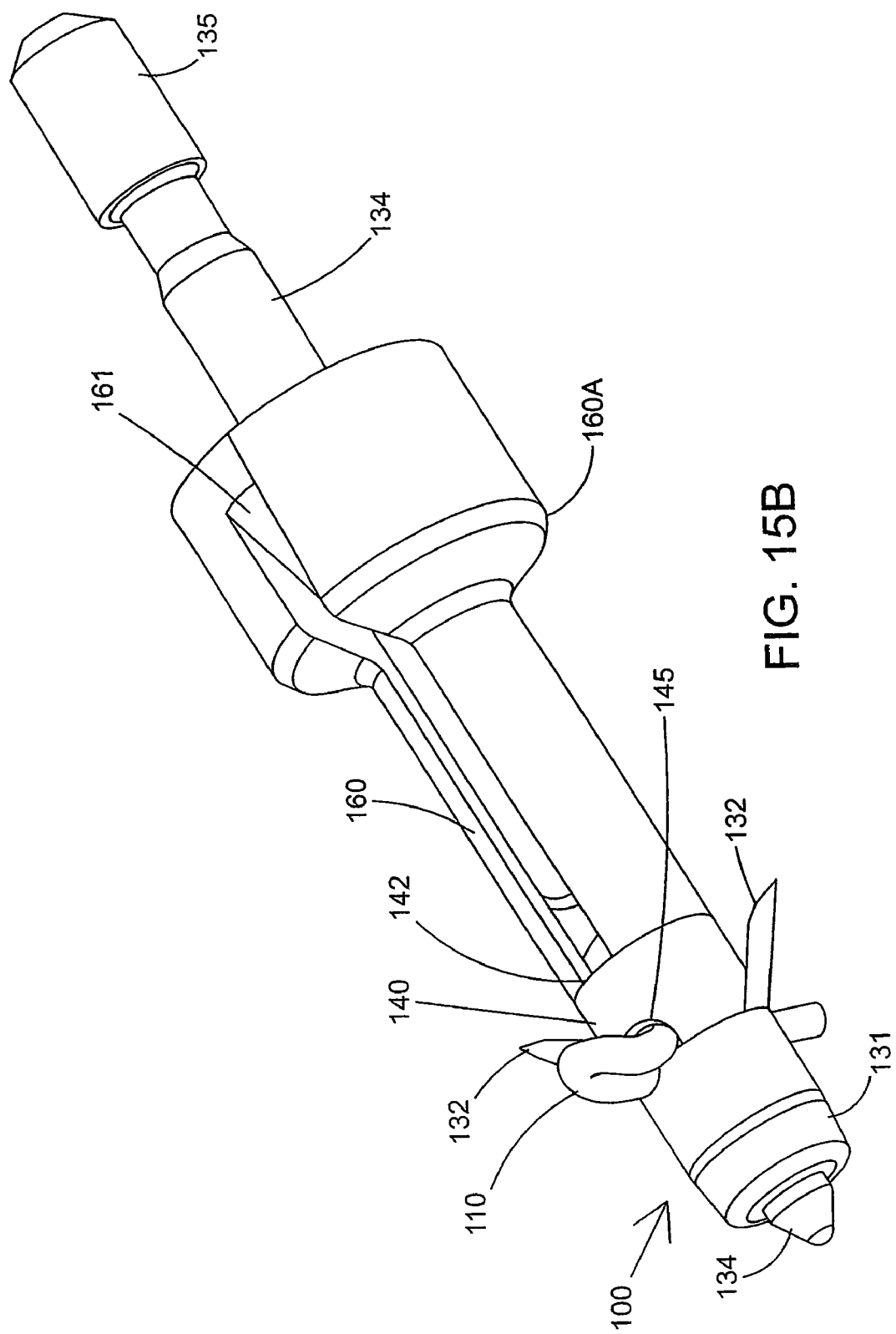
FIG. 15B is a perspective view showing the suture anchor in its deployed state.
Figure 17:
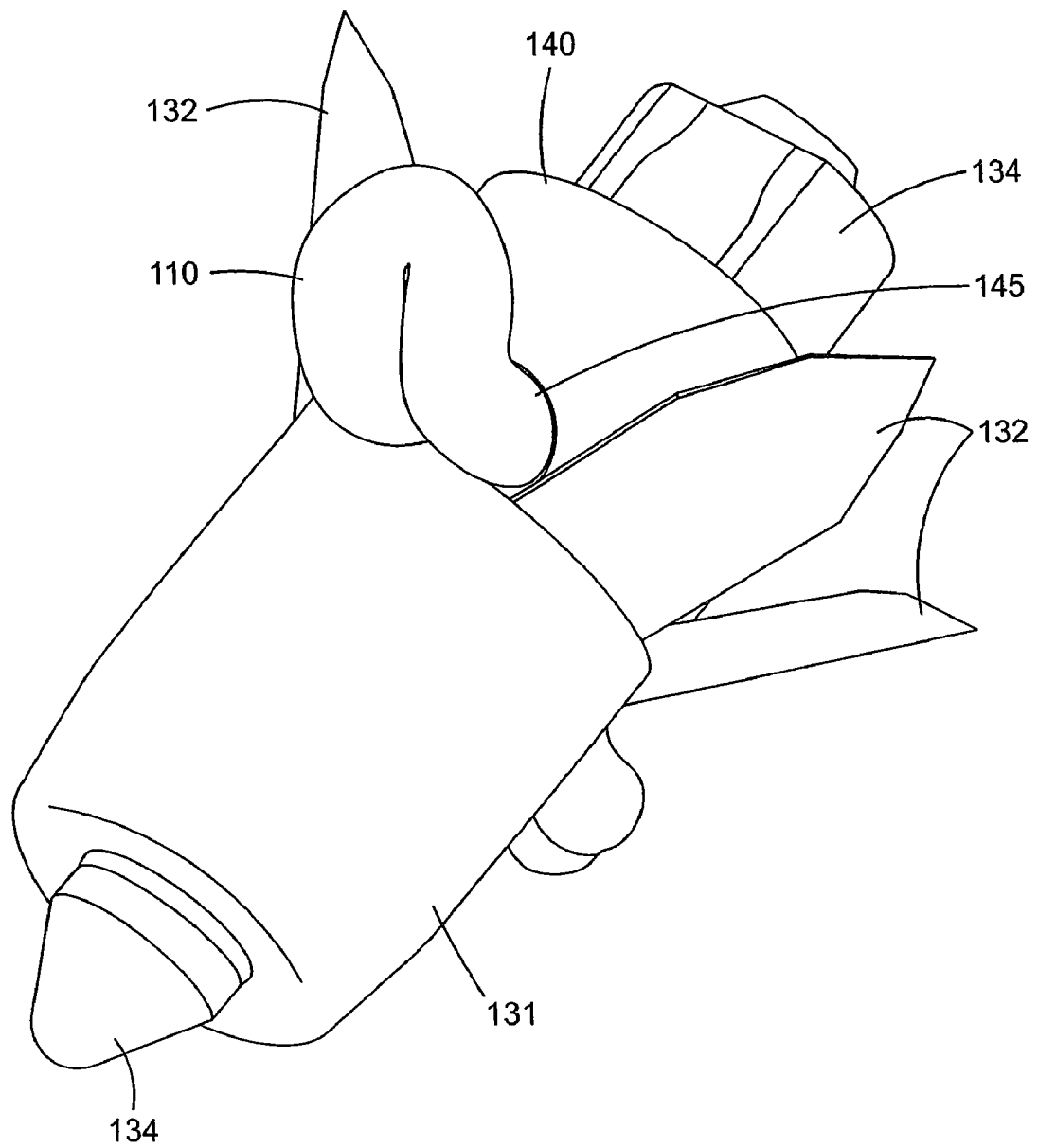
FIG. 17 is a further rotated view of the suture anchor of FIG. 16 in its deployed state.

The suture anchor 100 having the suture ends inserted through the opening 112 and having tissue 200 attached to the suture by the loop L thus formed, is thereafter inserted into the borehole in the bone using a known insertion tool 150. Tension, as shown by the arrow 115 in FIG. 11B, is applied to the suture to draw up the tissue 200 to the anchor implant site in the bone. As shown in FIG. 12, the anchor is then activated using tool 150 by applying force F to shaft 134. To activate the anchor, the tool 150 applies an axial tensile force to the shaft 134 of the anchor by engaging the shoulder portion 135. The borehole in the bone is not shown in these drawing figures. When the anchor is activated, the opening 112 in the shaft 134 moves proximally, thereby securely clamping the two suture 110 portions between member 140 and distal end 112A (See FIGS. 11A and 13) of aperture 112 in shaft 134 in a U-shaped path. Member 140 is provided with a rounded recess 145 to comfortably receive the suture 110 and prevent cutting of the clamped suture. The anchor crown portion 131 has a plurality of proximally extending penetrating fingers 132 which are adapted to penetrate into the borehole formed previously in the bone to which the tissue 200 is to be attached. Upon activation of the anchor once in the borehole in the bone, the fingers 132 extend radially outwardly and penetrate into the bore hole thus securing the anchor and thus the suture to the bone. The penetrating fingers 132 are splayed radially outwardly, as shown in FIG. 12 as they engage against the cam surface 133 of portion140. The suture 110 is securely clamped in the opening 112 in the shaft portion 134 between distal end 112A of opening 112 and the member 140 of the anchor (and thus between crown portion 131 and member 140). This securely fastens the soft tissue 200 proximate the bone.

FIGS. 13, 14B, 15B, 16 and 17 show the anchor after deployment. In these views, the tissue 200 is not shown for clarity.

After the anchor is activated and the suture is secured, with the soft tissue 200 being secured proximate the bone, the anchor 100 and, in particular, the anchor portions 131, 140 and the distal portion of shaft 134 secured to these portions are released from a discardable proximal portion 134A of the shaft 134, typically through a frangible connection 142 (See FIG. 11B), as known to those of skill in the art. The tool for activating the anchor is not shown fully but is known to those of skill in the art and is generally used with anchors of the type shown in the drawings. A portion of the tool is shown at 150 only schematically. Once the shaft breaks at 142, the proximal portion 134A of the shaft 134 to the right of connection 142 in FIGS. 11 and 12 breaks away from the portions of the suture anchor 131, 140 and the distal-most portion of shaft 134 attached to crown portion 131, remain in the borehole. The portion 160 and shaft portion 134A to the right of joint 142 are discarded.

Portion 160 includes an enlarged diameter portion, which enlarges at 160A. Portion 160 also includes recesses 161 provided longitudinally therein for routing free ends of the suture 110.

The embodiments previously described require that both ends of the suture be threaded through the opening or openings in the anchor after the suture has been passed through the tissue to be attached or reattached. An embodiment will now be described wherein it is only necessary to thread one end of the suture through the anchor.

Figure 18:
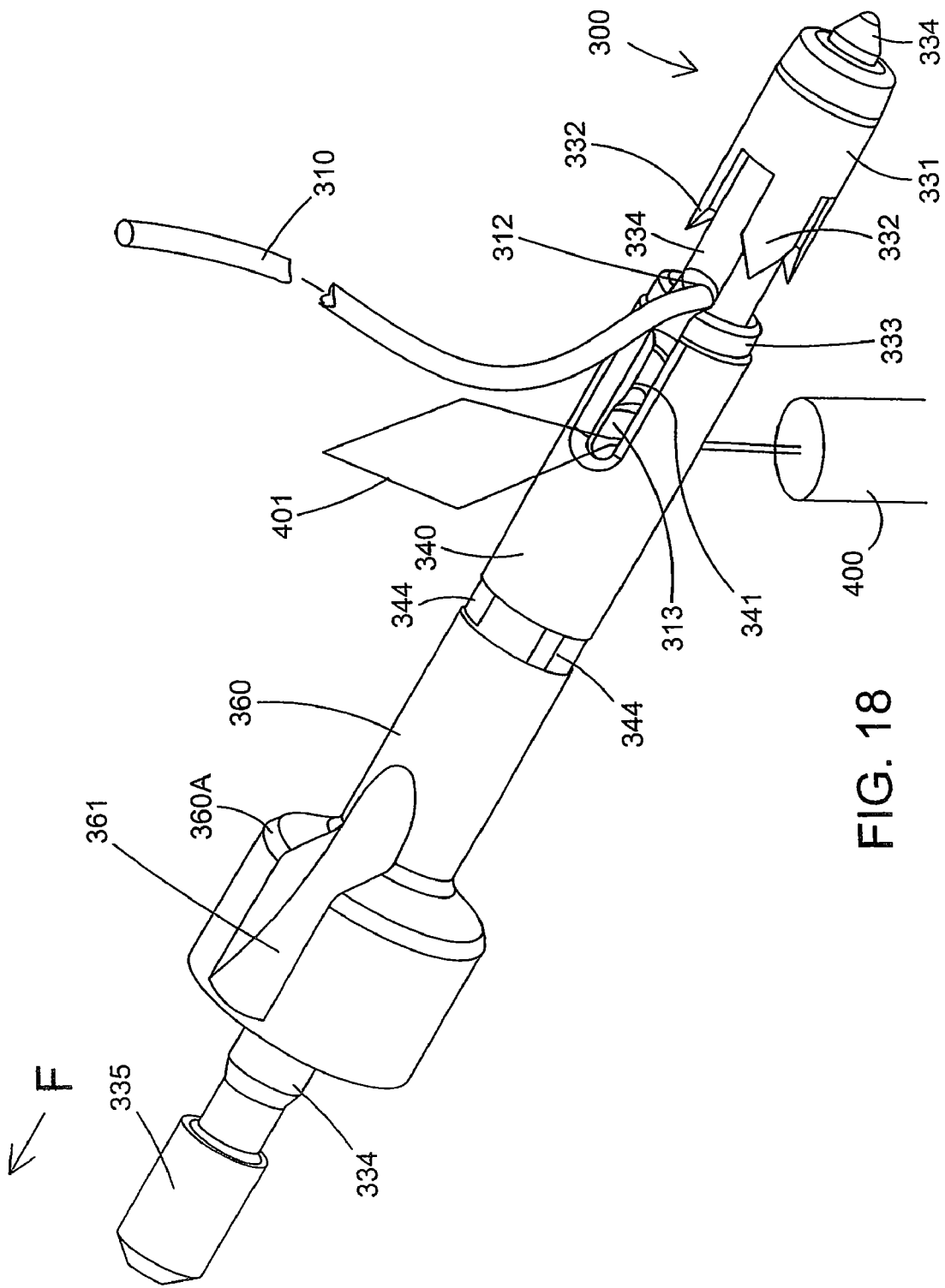
FIG. 18 show a third embodiment of a suture anchor according to the present invention wherein one end of a suture is provided attached to the suture anchor and also showing a threading tool inserted through an aperture of the suture anchor.
Figure 18A:
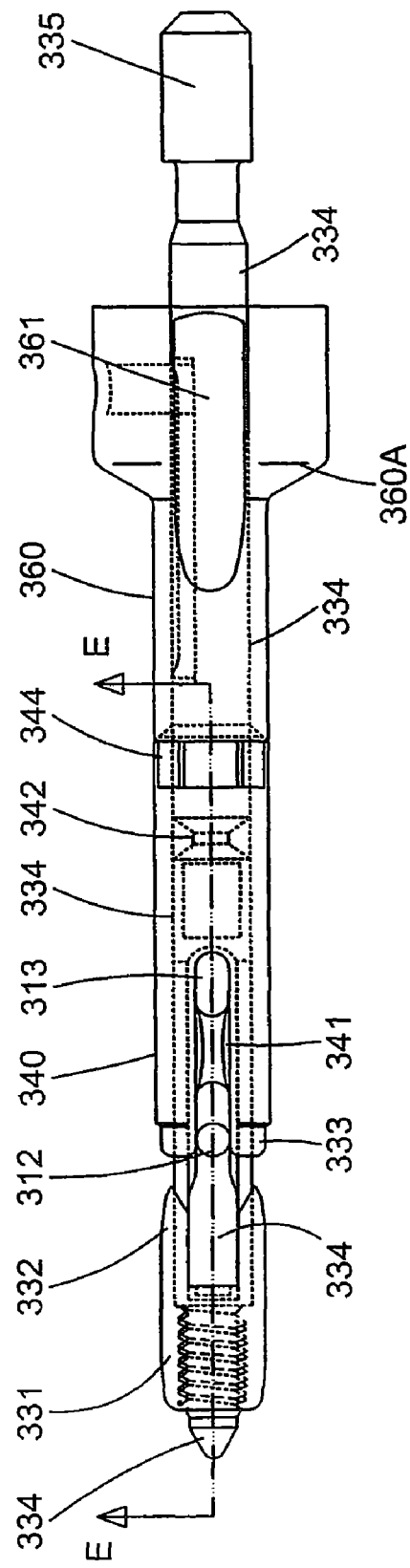
FIG. 18A shows the suture anchor of FIG. 18 in phantom view.
Figure 18B:
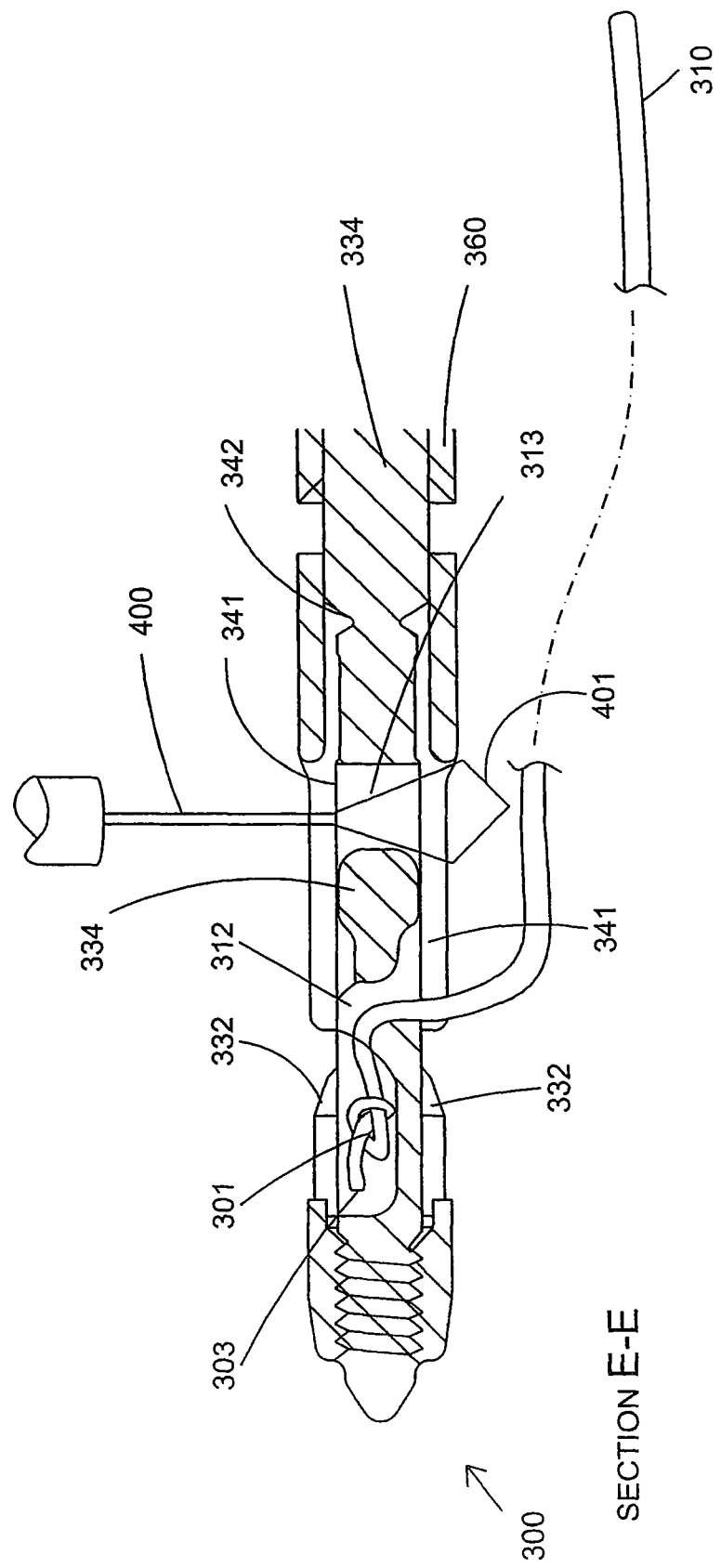
FIG. 18B shows details of the suture anchor of FIG. 18A along lines E-E of FIG. 18A and prior to threading the suture through tissue and back through the suture anchor.

Turning now to FIGS. 18-23, a third embodiment of the suture anchor and method according to the present invention is described. In this embodiment, one end of the suture 310 is permanently affixed to the anchor, the anchor being generally shown at 300. The fixation of the suture 310 to the anchor 300 may be by any suitable means, for example, a knot 301 as shown in FIG. 18B or any other suitable securement, for example, a frictional or clamping securement. The anchor 300 is similar to the anchor of the second embodiment and includes a crown portion 331 including deformable fingers 332. The shaft 334 is coupled to the crown portion 331 as in the second embodiment, e.g., by threads. Alternatively, shaft 334 need not be secured to crown portion 332, but can instead have a shoulder (like shoulder 13 of the embodiment of FIG. 1) for abutting against crown portion 331 and applying a force thereto to deploy the fingers of the crown portion. This is also true of the second embodiment. A cam surface 333 is provided on outer cylindrical clamping portion 340 as in the second embodiment. The shaft 334 has a proximal end 335 which is engageable by the insertion tool for the application of a tensile force in direction F on the shaft 334. The shaft 334 moves coaxially in the outer cylinders 340 and 360, as in the second embodiment. Portion 360 is provided with a cutout or cutouts 361 for routing the suture, as in the second embodiment. Widened diameter stop shoulder 360A is provided, as in the second embodiment, to limit insertion in the tissue borehole.

Figure 19:
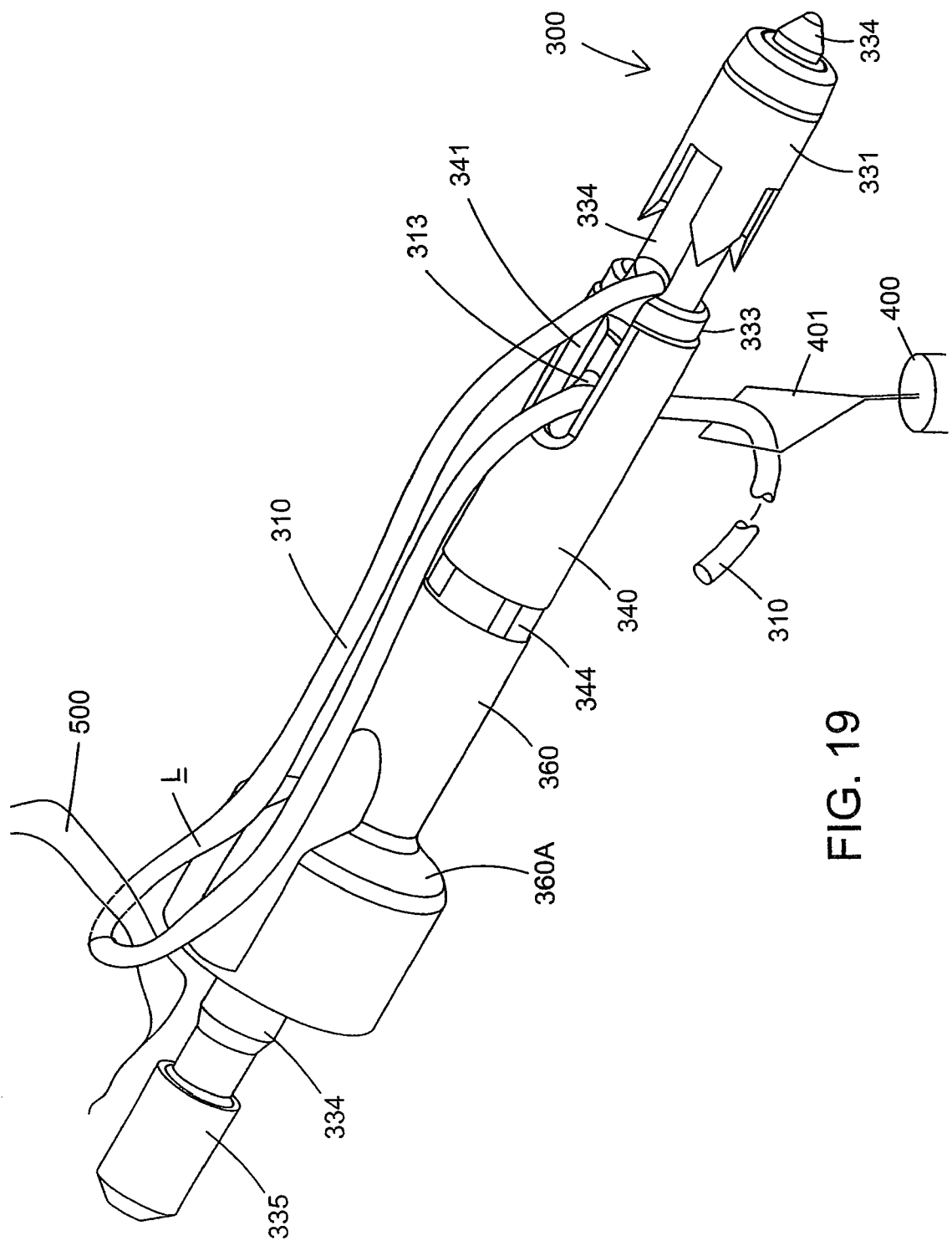
FIG. 19 shows the third embodiment of the suture anchor after it has been threaded through tissue to be attached by the suture anchor to tissue in which the anchor is to be installed and after threading the suture through an aperture in the anchor.

As shown in FIG. 18B, the suture 310 may be held in the shaft portion 334 of the anchor 300 by any suitable means, for example a knot 301 disposed in a recess 303. The suture 310 extends through a serpentine recess 303A (FIG. 19A) in shaft 334, through an opening 312 provided in the shaft portion 334 and thence thorough an elongated opening 341 provided in the outer cylindrical clamping portion 340. The knot 301 is retained in position between the recess in the shaft and the crown portion 331, which acts as a retainer member. As shown in FIG. 18 and FIG. 18B, a threading tool 400 having a threading loop 401 is inserted through the opening 341 in the outer cylindrical portion 340 and through another aperture 313 provided in the shaft 334. The suture 310, as shown in FIG. 19, is threaded through the tissue 500 which is to be attached or reattached to the tissue in which the anchor 300 is to be inserted. The suture 310 is thereafter fed through the loop 401 in known fashion, and the loop 401 is then withdrawn as shown in FIG. 19 through the aligned openings 341 and 313 to thereby draw the suture 310 through the anchor, as shown in FIG. 19. In contrast to the embodiments previously described, only one end of the suture 310 needs to be threaded through the anchor, the other end being securely fastened to the anchor, for example, by knot 301. The suture 310 may be supplied already attached at 301 to anchor 300 upon purchase. In the drawing figures, the threading loop 401 is shown in much closer proximity to the tissues than would be encountered in actual practice.

Figure 19A:
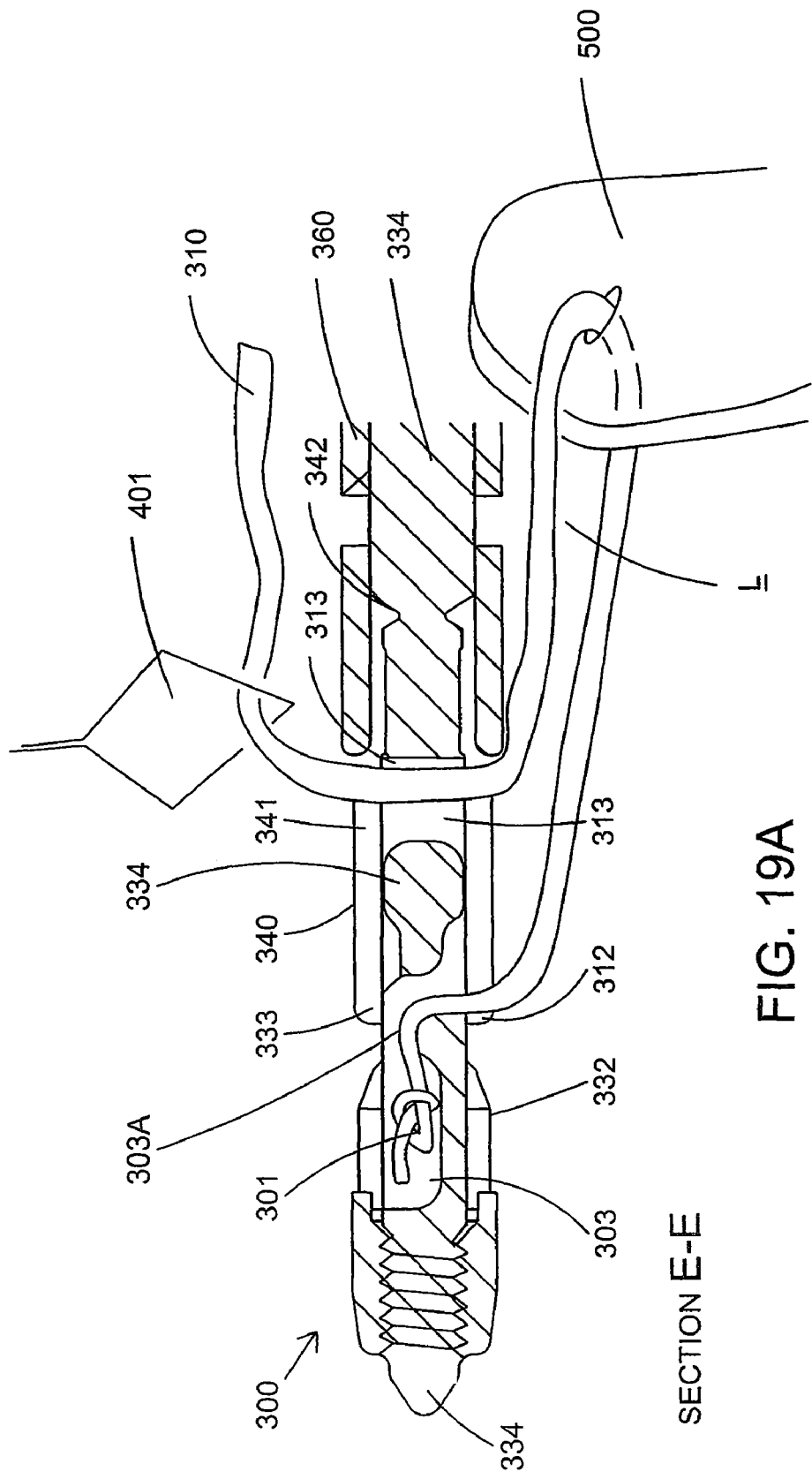
FIG. 19A shows the suture anchor also along lines E-E of FIG. 18A after the suture has been threaded through the tissue and through an aperture in the suture anchor.

Turning to FIG. 19A, which shows the suture 310 threaded through the openings 341 and 313, the suture threader 401 is now withdrawn from the suture 310 and the anchor 300 is now ready to be installed in the borehole in the tissue to which the tissue 500 is to be reattached. The tissue 500 is now attached to the anchor 300 via the suture loop L.

The anchor 300 with tissue 500 attached is now inserted in the bone borehole. Tension is applied to the one free end of the suture 310 to snug tissue 500 to the anchor insertion site.

Figure 20:
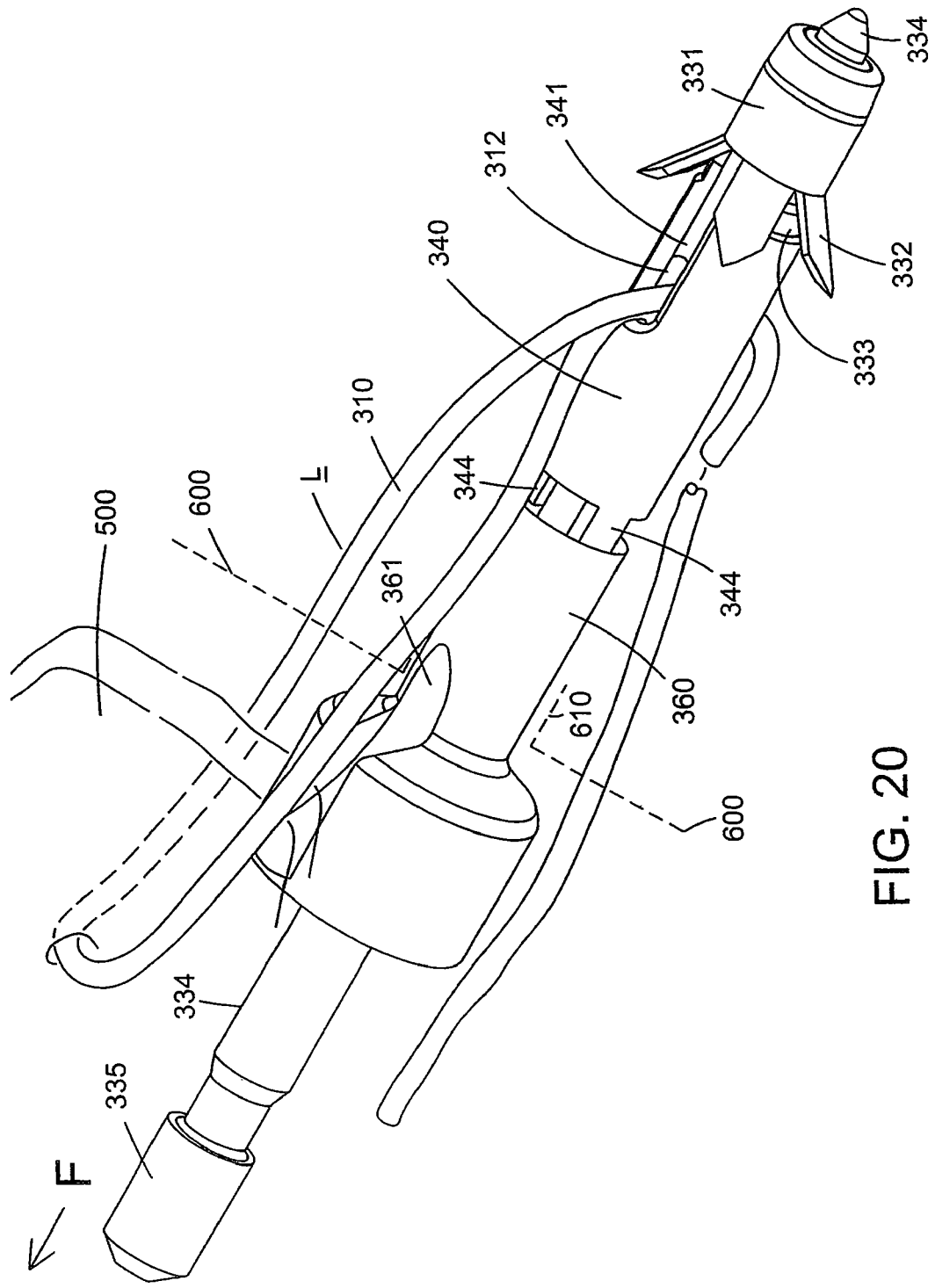
FIG. 20 shows the third embodiment of the suture anchor after it has been inserted into and deployed in a bore hole in tissue such as bone and showing the soft tissue in an attached state against the bone.

As shown in FIG. 20, a force in direction F is applied by the insertion tool to the proximal end 335 of the shaft 334, causing the crown portion 331 of the suture anchor to move with respect to the cam surface 333, thereby splaying the fingers 332 radially outwardly in the proximal direction. The bone is shown schematically by broken lines 600 and the borehole is shown at 610.

When the suture anchor 300 is deployed in the tissue by actuation of the insertion tool, the shaft portion 334 moves proximally with respect to the portions 340 and 360. The fingers 332 cam against the cam surface 333 of the portion 340, causing the fingers 332 to splay radially outwardly in the proximal direction. At the same time, the shaft 334 moves with respect to the outer cylindrical portion 340, causing the suture 310 to be pinched along a convoluted path as best shown at 350 in FIG. 20B, between the portion 340 and the shaft 334. Portion 340 thus acts to clamp the suture 310 between itself and shaft 334. Opening 313 of shaft 334 is thus covered by clamping portion 340. The spacing between outer cylindrical clamping portion 340 and shaft 334 at 350 is made such that a force fit is obtained of the suture between the portion 340 and shaft 334. Preferably, the spacing between shaft 334 and portion 340 is such that shaft 334 at this location has an outside diameter so that the spacing on two opposed sides of shaft 344 between the inside diameter of portion 340 and the outside diameter of shaft 334 is slightly less than the thickness of the suture employed. Thus, a force fit of the suture within the anchor is obtained, securely fastening the tissue 500 to the looped suture L between the knotted end 301 of the suture and the end of the suture secured at convoluted path 350 in the anchor. In addition to the force fit of the suture at 350, the convoluted path at 350 provides added securement.

Prior to actuation of the insertion tool, the surgeon will exert a suitable tension force to the free end of the suture to draw the tissue 500 proximate the attachment site, i.e. so that the tissue 500 overlays the bone.

Figure 21:
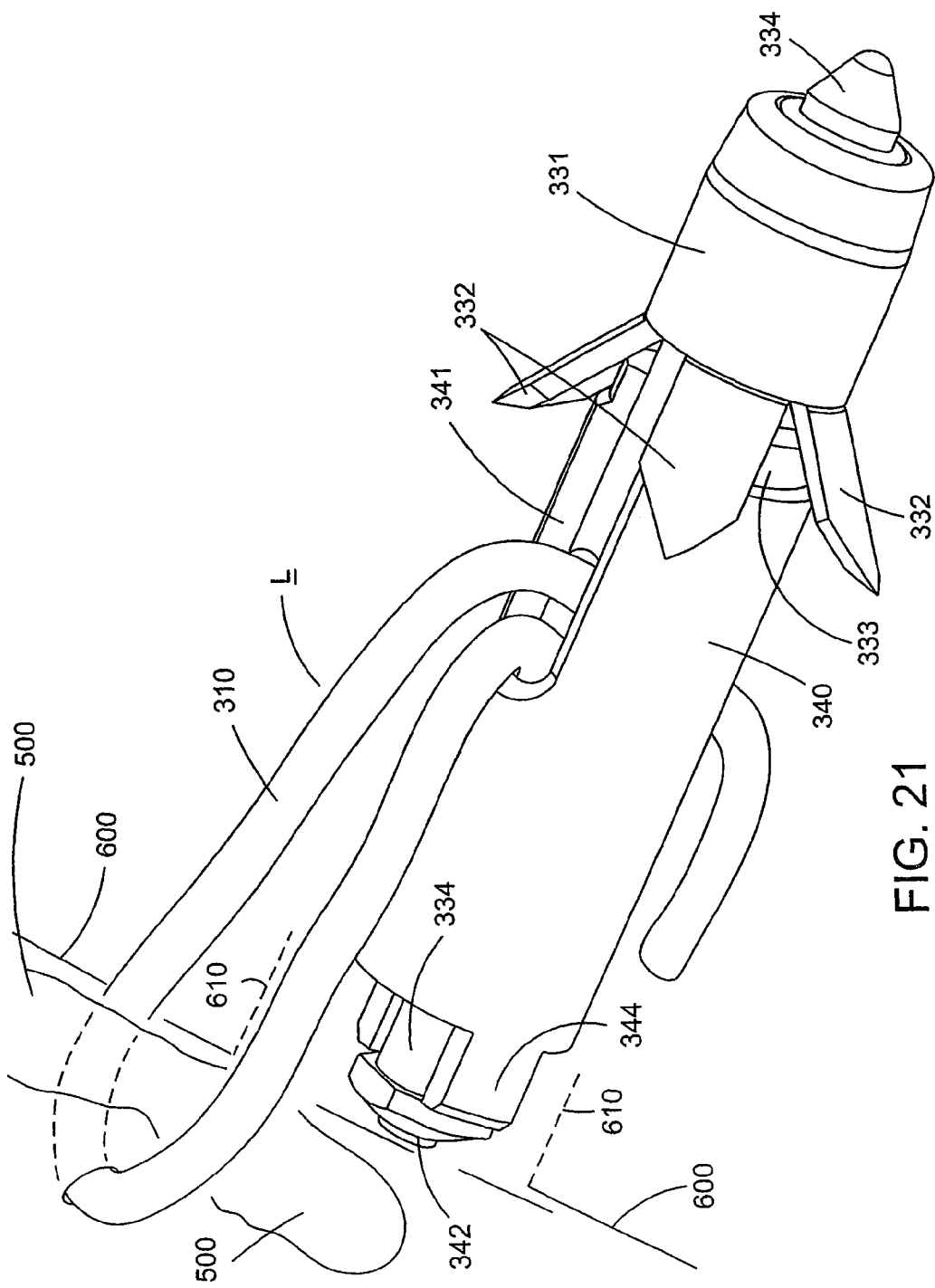
FIG. 21 shows the suture anchor according to the third embodiment in its deployed state after a disposable portion of the suture anchor has been removed.
Figure 21A:
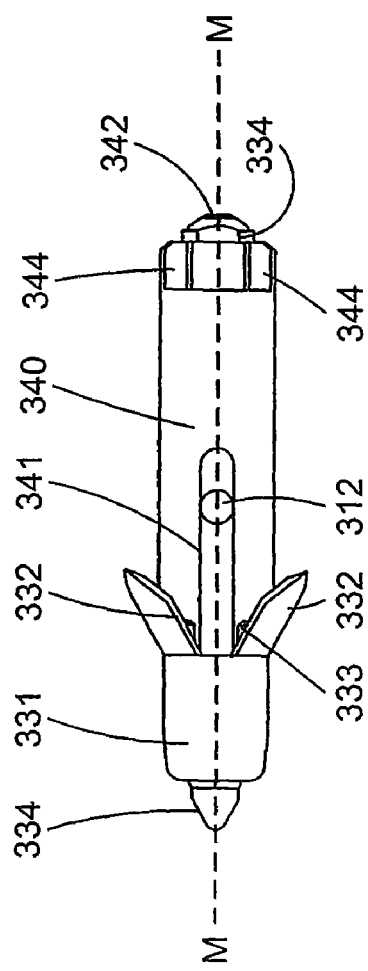
FIG. 21A is a plan view of the suture anchor of FIG. 21 according to the third embodiment in its deployed state.
Figure 21B:
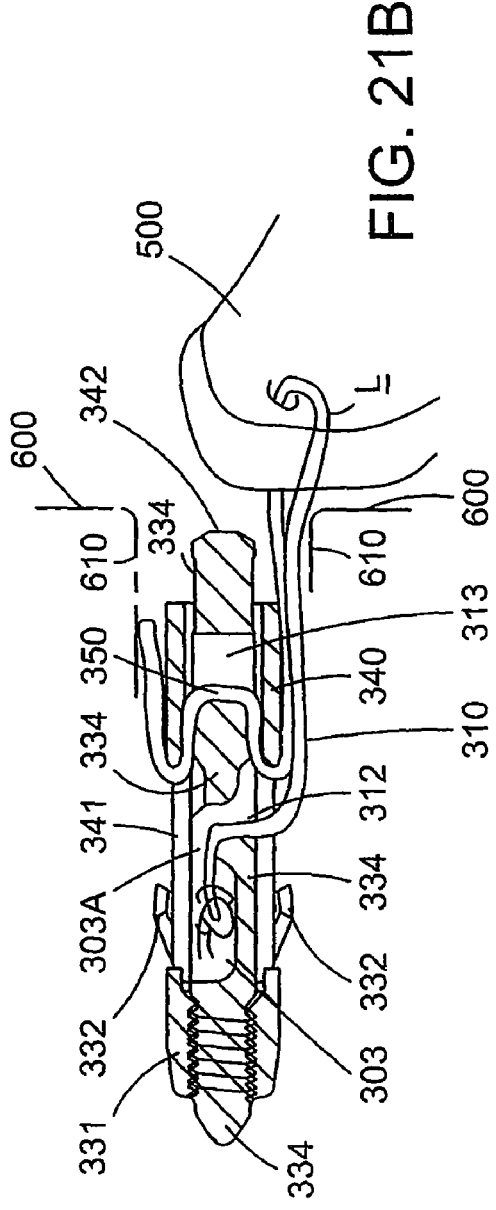
FIG. 21B is a sectional view of the suture anchor of FIG. 21A in its deployed state along lines M-M of FIG. 21A.

As in the second embodiment, once suitable activation force is applied by the insertion tool to the shaft 334, the shaft 334 breaks at the frangible connection 342, thereby separating the disposable portion of the anchor (the shaft 334 to the right of frangible connection 342 and member 360 as shown in FIG. 20B). As in the other embodiments, frangible connector 342 may be formed as a weakened point in shaft 342, such as a score line or portion of reduced thickness. FIG. 21 shows the suture anchor according to the third embodiment deployed in the borehole after removal of the disposable portion, which, of course, is attached to the insertion tool and is removed when the insertion tool is withdrawn. For clarity, the loop L has been shown somewhat expanded in FIG. 21. When the anchor is placed in the borehole 610, the suture loop L would be located close to the anchor between the anchor and the borehole.

As shown in FIG. 22B, and in detail in FIG. 22C, in order to ensure that shaft portion 334 and outer cylindrical clamping portion 340 are securely locked together when the anchor is deployed, thereby to prevent portions 331 and 340 from moving with respect to each other after securement in the borehole, a cam surface 363 may be provided on distal edge of portion 360 as shown in FIG. 22. Cam surface 363 is formed with an inwardly proximally inclined surface which engages with fingers 344 of portion 340, thereby causing fingers 344 to move radially inwardly as shaft 334 moves proximally during actuation. This causes the ends of fingers 344 to seat securely against a shoulder 337 provided on the shaft 334. This helps to prevent shaft 334 from moving with respect to outer portion 340, thereby securely holding the portions 340, 331 and 334 in secure engagement, and preventing the suture 310 from detachment from the anchor 300 at convoluted path 350.

Figure 23A:
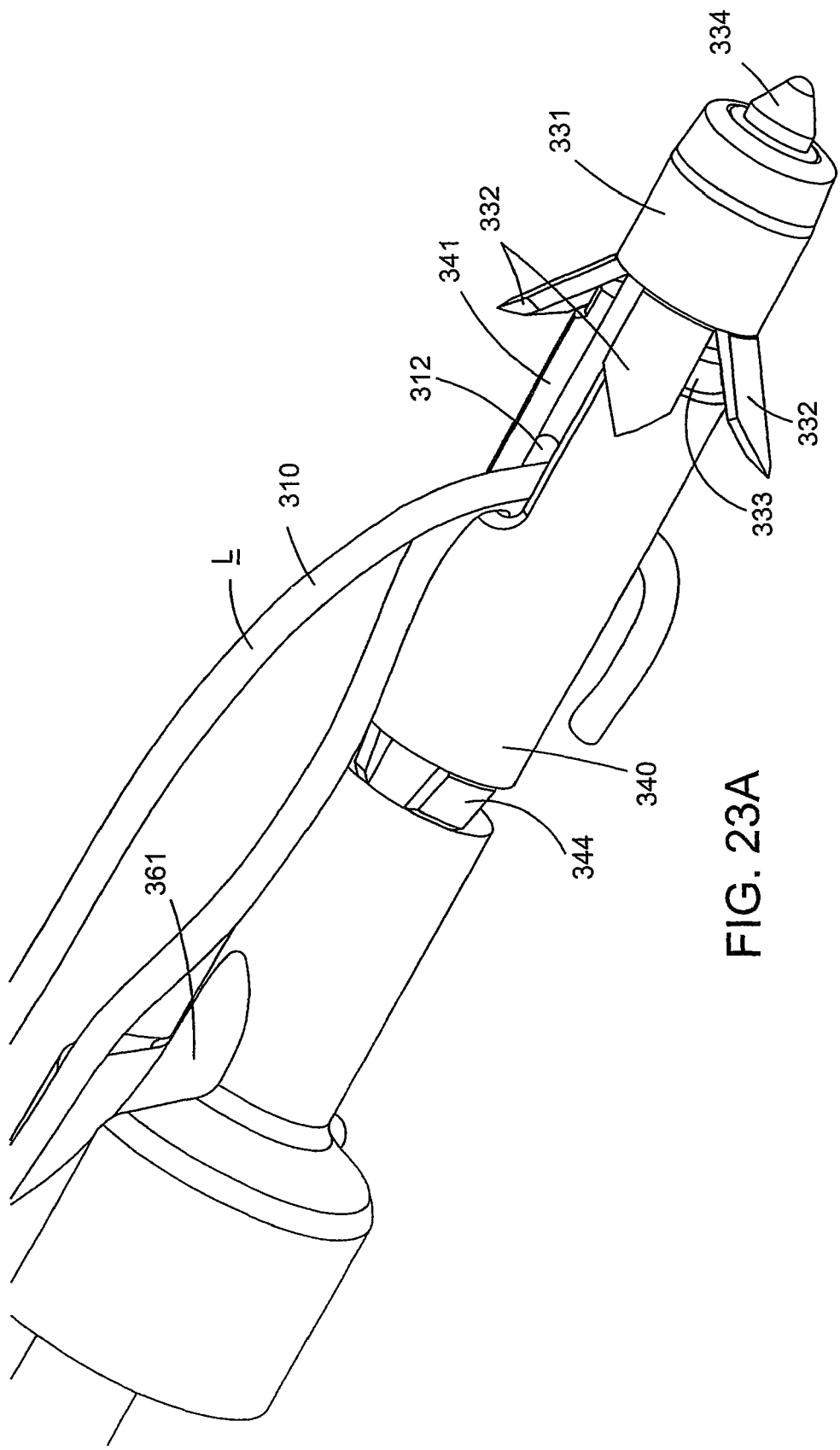
FIG. 23A is a perspective view of the suture anchor of FIG. 22 in its deployed state prior to rupture of the frangible connection.
Figure 23B:
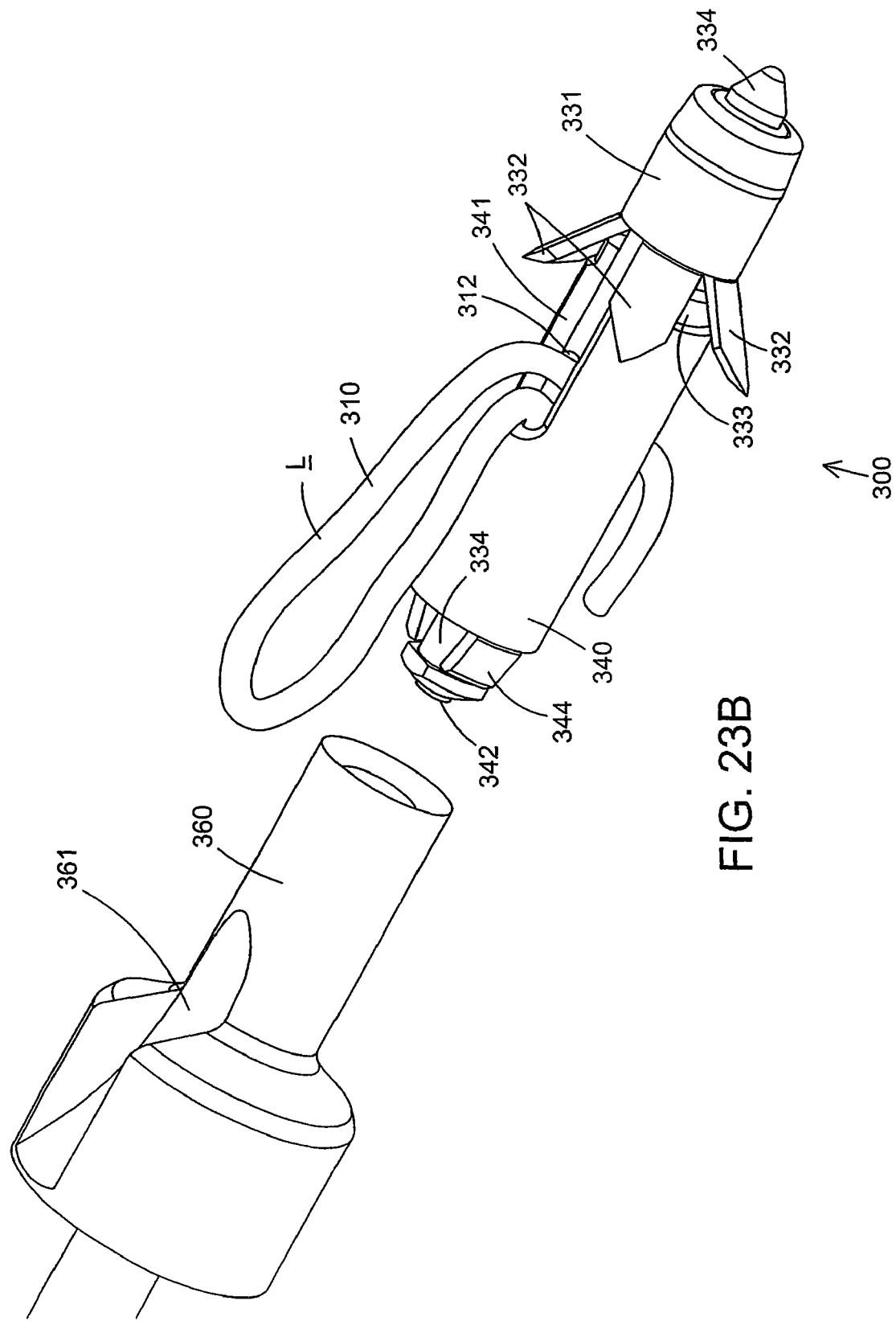
FIG. 23B shows the suture anchor of FIG. 23A after removal of the discarded portion of the anchor.

FIG. 23B shows the suture anchor after rupture at the frangible connection 342. For clarity the two tissue members being attached have not been shown in that figure.

The third embodiment has advantages over the other two embodiments, particularly in that it is simpler to use since only one suture end needs to be threaded through the opening in the anchor once the suture has been threaded through the tissue which is to be attached or reattached to the tissue in which the anchor is to be installed.

The embodiment shown in FIG. 22 utilizes the crimping of the fingers 344 to hold the portion 340 more securely to the shaft 334. This represents a modification of the embodiment shown in FIG. 21 wherein crimping of the fingers 344 is not employed. In that embodiment, the fingers 344 rest against the shoulder 337 but are not crimped inwardly. The embodiment shown in FIG. 22 provides an additional degree of securement of the portions 340 and 334. It should also be noted that the first two embodiments may also employ a suitable means, such as fingers 344, to ensure that the various parts of the anchor remain securely fastened together after deployment.

Although the present invention has been described in relation to particular embodiments thereof, many other variations and modifications and other uses will become apparent to those skilled in the art. Therefore, the present invention should be limited not by the specific disclosure herein, but only by the appended claims.

What is claimed is:

1. A method for knotlessly securing first and second tissues with a suture anchor comprising the steps of:
    forming a borehole in the first tissue;
    threading a suture through the second tissue forming a loop in the suture with the tissue thereby secured in the loop, the loop defining two suture portions;
    attaching the two suture portions to the anchor whereby the two suture portions are threaded through the anchor and initially movable with respect to the anchor;
    providing a force to a shaft of the anchor, the force causing clamping of the two suture portions in the anchor and deformation of a deformable portion of the anchor to cause the deformable portion to engage a wall of the borehole thereby to secure the suture anchor in the first tissue and the loop holding the second tissue to the suture anchor, further wherein the clamping comprises providing a spacing between two clamping members in the anchor wherein the two suture portions are received, moving the clamping members relatively with respect to each other to close the spacing and clamp the two suture portions between the clamping members, thereby frictionally engaging the two suture portions between the clamping members when the force is applied to the suture anchor;
    further comprising providing a convoluted path for the two suture portions in the anchor to assist in securement of the suture portions in the suture anchor; and
    further wherein the path is U-shaped.

2. The method of claim 1, wherein the step of attaching comprises threading the two suture portions through an opening in the shaft and the clamping comprises clamping the two suture portions between the clamping members comprising the opening in the shaft and an outer cylindrical portion of the suture anchor.

3. The method of claim 2, wherein the step of clamping comprises moving the shaft proximally to cause deformation of the deformable portion, and clamping the two suture portions between a wall of the opening and the outer cylindrical portion disposed proximally with respect to the deformable portion and coaxially about the shaft.

* * * * *